United States Patent
Yamashita et al.

(10) Patent No.: US 10,431,066 B2
(45) Date of Patent: Oct. 1, 2019

(54) TERMINAL APPARATUS AND TERMINAL PROCESSING METHOD FOR OBJECT MONITORING SYSTEM, CENTRAL PROCESSING APPARATUS AND CENTRAL PROCESSING METHOD FOR OBJECT MONITORING SYSTEM, AND OBJECT MONITORING SYSTEM

(71) Applicant: Konica Minolta, Inc., Tokyo (JP)

(72) Inventors: Masanori Yamashita, Toyonaka (JP); Aki Tsuji, Kyoto (JP); Atsuhiro Noda, Ashiya (JP)

(73) Assignee: Konica Minolta, Inc., Tokyo (JP)

( * ) Notice: Subject to any disclaimer, the term of this patent is extended or adjusted under 35 U.S.C. 154(b) by 0 days.

(21) Appl. No.: 16/229,378

(22) Filed: Dec. 21, 2018

(65) Prior Publication Data

US 2019/0122520 A1    Apr. 25, 2019

Related U.S. Application Data

(62) Division of application No. 15/561,850, filed as application No. PCT/JP2016/056471 on Mar. 2, 2016, now Pat. No. 10,198,926.

(30) Foreign Application Priority Data

Mar. 26, 2015    (JP) ................. 2015-065285

(51) Int. Cl.
   *G08B 21/02*    (2006.01)
   *A61G 12/00*    (2006.01)
   (Continued)

(52) U.S. Cl.
   CPC ........ *G08B 21/0294* (2013.01); *A61B 5/1113* (2013.01); *A61G 12/00* (2013.01);
   (Continued)

(58) Field of Classification Search
   CPC .......................... A61B 5/7264; G06F 19/3418
   See application file for complete search history.

(56) References Cited

U.S. PATENT DOCUMENTS

2007/0118054 A1*    5/2007    Pinhas ................. A61B 5/1104
                                                600/587
2008/0058616 A1*    3/2008    Nakagawa ........... A61B 5/0006
                                                600/301
(Continued)

FOREIGN PATENT DOCUMENTS

JP    2014-057180 A    3/2014
JP    2014-090913 A    5/2014
(Continued)

OTHER PUBLICATIONS

Official Action issued in corresponding JP Application No. 2018-111855 dated Feb. 21, 2019.
(Continued)

*Primary Examiner* — Fabricio R Murillo Garcia
(74) *Attorney, Agent, or Firm* — Baker Hostetler

(57) ABSTRACT

A terminal apparatus and method therefor according to the present invention are an apparatus and method for receiving and displaying monitoring information in an object monitoring system for sensing and monitoring an object, have a plurality of operation modes including a condition check mode of checking a condition of the object until receiving an intention to actually perform an action on the object after receiving the monitoring information, and prohibit executing the condition check mode on the object when a condition of the object is being checked by other apparatus in the condition check mode. The present invention relates to an object monitoring system using the terminal apparatuses, and a central processing apparatus and central processing method therefor.

17 Claims, 12 Drawing Sheets

(51) Int. Cl.
*A61B 5/11* (2006.01)
*G08B 21/04* (2006.01)
*A61B 5/00* (2006.01)
*G06T 13/80* (2011.01)

(52) U.S. Cl.
CPC ....... *G08B 21/043* (2013.01); *G08B 21/0423* (2013.01); *G08B 21/0476* (2013.01); *A61B 5/1115* (2013.01); *A61B 5/742* (2013.01); *A61B 5/7475* (2013.01); *G06T 13/80* (2013.01); *G06T 2210/41* (2013.01); *G08B 21/02* (2013.01)

(56) References Cited

U.S. PATENT DOCUMENTS

| | | | | |
|---|---|---|---|---|
| 2008/0214904 | A1* | 9/2008 | Saeed | A61B 5/0006 600/301 |
| 2010/0106524 | A1* | 4/2010 | Wu | G06Q 40/08 705/3 |
| 2012/0065477 | A1 | 3/2012 | Enomoto | |
| 2015/0297078 | A1* | 10/2015 | Gross | G06F 19/3418 340/870.07 |
| 2017/0116377 | A1 | 4/2017 | Kitagawa | |

FOREIGN PATENT DOCUMENTS

| | | |
|---|---|---|
| JP | 2014-158228 | 8/2014 |
| JP | 2014-158228 A | 8/2014 |
| JP | 2014-158637 A | 9/2014 |
| JP | 2014-171055 A | 9/2014 |
| JP | 2014-204752 A | 10/2014 |
| JP | 2014-210026 A | 11/2014 |

OTHER PUBLICATIONS

International Patent Application No. PCT/JP2016/056471; Int'l Written Opinion and the Search Report dated May 17, 2016; 7 pages.

* cited by examiner

| SENSOR ID 4231 | DETERMINATION RESULT 4232 | DETERMINATION TIME (RECEPTION TIME) 4233 | STILL IMAGE (FILE NAME) 4234 | ANIMATION (IP ADDRESS) 4235 | CONDITION CHECKING 4236 | ACTION 4237 |
|---|---|---|---|---|---|---|
| SU-1 | WAKE-UP | 06:32 | SP1 | .*.*. | 0 | 0 |
| SU-1 | RISING | 06:45 | SP2 | .*.*. | 0 | 0 |
| ... | ... | ... | ... | ... | ... | ... |
| ... | ... | ... | ... | ... | ... | ... |
| ... | ... | ... | ... | ... | ... | ... |

B.

DT

| SENSOR ID 4241 | INSTALLATION PLACE 4242 | OBJECT NAME 4243 |
|---|---|---|
| SU-1 | 101 | MKAWA KKO |
| SU-2 | 102 | KYAMA MTA |
| ... | ... | ... |
| ... | ... | ... |

TERMINAL APPARATUS AND TERMINAL PROCESSING METHOD FOR OBJECT MONITORING SYSTEM, CENTRAL PROCESSING APPARATUS AND CENTRAL PROCESSING METHOD FOR OBJECT MONITORING SYSTEM, AND OBJECT MONITORING SYSTEM

This application is a divisional application of U.S. application Ser. No. 15/561,850, filed Sep. 26, 2017, which is a 371 application of PCT/JP2016/056471, filed Mar. 2, 2016, which claims priority to Japanese Application No. 2015-065285, filed Mar. 26, 2015, the disclosures of which are hereby incorporated in their entireties.

TECHNICAL FIELD

The present invention relates to a terminal apparatus and terminal processing method for an object monitoring system for monitoring an object to be monitored by use of a plurality of devices, a central processing apparatus and central processing method for the object monitoring system, and the object monitoring system.

BACKGROUND ART

Our country (Japan) is an aging society, more specifically a super-aging society in which the percentage of the population aged 65 or older relative to the total population is over 21% due to improvement in living standards along with rapid economic growth after the war, improvement in public health, improvement in healthcare standards, and the like. Further, the population aged 65 and older relative to the total population of about 127.65 million is about 25.56 million in 2005, while the population aged 65 and older relative to the total population of about 124.11 million is estimated as large as about 34.56 million in 2020. In such an aging society, the persons in need of nursing or care due to illness, injury, advanced age, and the like are estimated as more than the persons in need of nursing in an ordinary society which is not an aging society. Additionally, our country is also a low-birthrate society in which the total fertility rate is 1.43 in 2013, for example. Thus, there is being caused a situation in which an aged family member (spouse, son or daughter, or sibling) cares for an elder person in need of nursing.

A person in need of nursing receives nursing or care in a hospital or a facility such as welfare center for the aged (such as short-stay facility for the aged, nursing home for the aged, and special nursing home for the aged under Japanese laws). In such facilities, there is caused a case in which a person in need of nursing is injured due to falling out of a bed or falling during walking, or slips out of a bed and walks round. Such a case needs to be handled as soon as possible. Further, such a situation can be more serious if it is left unsolved. Thus, nurses and careworkers check the safety and conditions of the persons in need of nursing by periodically going the rounds of them in the facilities.

However, the nurses and the like do not sufficiently increase for an increase in the persons in need of nursing, and the business field of nursing and cares is always lack of workers. Further, a less number of nurses and careworkers work in twilight shift or night shift than in day shift and an individual working load increases, and thus the working loads need to be alleviated. Further, a situation in which an aged nurse or the like cares for an aged person in need of nursing is often caused in the facilities. An elder person is generally weaker, and thus an elder nurse bears a heavier load on nursing and the like than a younger nurse and his/her motions and judgements are slower even if he/she is healthy.

There is required a technique for complementing the nursing works or care works in order to eliminate the shortage of workers and to alleviate the burdens on the nurses. Thus, in recent years, there have been studied and developed object monitoring techniques for monitoring objects to be monitored such as persons in need of nursing.

As one of the techniques, there is a nurse call system disclosed in Patent Literature 1, for example. The nurse call system disclosed in Patent Literature 1 is a nurse call system having a nurse call child machine installed by a bed and used by a patient for calling a nurse, and a nurse call parent machine installed at a nurse station and directed for answering the call by the nurse call child machine, the system having a camera for shooting the patient on the bed from above the bed and a state determination means for determining an occurrence of at least one of a state in which the patient sits up on the bed and a state in which the patient is away from the bed on the basis of a video shot by the camera, and outputting an attentional state occurring signal, in which the nurse call parent machine has a notification means for making a notification in response to the attentional state occurring signal.

On the other hand, persons living alone are similar to the persons in need of nursing in terms of safety check, and they are to be monitored.

When an object to be monitored is monitored by use of a plurality of devices, the monitoring result is transmitted to a plurality of terminal apparatuses, and while a terminal apparatus is checking a condition of the object, such as answering a nurse call, the fact is transmitted to the other terminal apparatuses. Thus, the user (monitoring person A) of the terminal apparatus handles the monitoring result, and thus the user (monitoring person B) of the other terminal apparatus tries to answer other monitoring result if any. The user (monitoring person A) of the terminal apparatus should perform an action (nursing, care, and help, for example) depending on the condition of the object based on the monitoring result, but when the user (monitoring person A) of the terminal apparatus only checks the condition of the object based on the monitoring result and does not perform the action depending on the condition of the object based on the monitoring result due to some cause, the user (monitoring person B) of the other terminal apparatus cannot recognize the situation and the action depending on the condition of the object based on the monitoring result can be delayed.

It is important to make accurate and rapid determinations and to handle in order to prevent accidents in the nursing work or care work, and there can arise a problem that a condition of an object can be severer when an accident which could have been prevented cannot be prevented due to delayed handling or when an action for trouble such as falling of the object is delayed.

CITATION LIST

Patent Literature

Patent Literature 1: JP 2014-90913 A

SUMMARY OF INVENTION

The present invention has been made in terms of the above situations, and it is an object thereof to provide a terminal apparatus and terminal processing method for an object monitoring system directed for enabling a checked condition of an object to be mutually shared and capable of performing an action depending on the condition of the object at a more accurate timing, a central processing apparatus and central processing method for the object monitoring system, and the object monitoring system.

A terminal apparatus and terminal processing method for an object monitoring system according to the present invention are directed for receiving and displaying monitoring information on an object in the object monitoring system for sensing and giving notification of a predetermined motion of the object and monitoring the object, in which a plurality of operation modes including a condition check mode of checking a condition of the object until receiving an intention to actually perform an action on the object based on the monitoring information after receiving the monitoring information are provided, and the condition check mode on the object based on the received monitoring information is prohibited from being executed while other terminal apparatus is checking the condition of the object based on the received monitoring information in the condition check mode. The present invention relates to an object monitoring system using the terminal apparatuses, and a central processing apparatus and central processing method. Therefore, the terminal apparatus and terminal processing method for an object monitoring system, the central processing apparatus and central processing method for the object monitoring system, and the object monitoring system enable a checked condition of an object to be mutually shared and an action depending on a condition of an object to be performed at a more appropriate timing.

The above and other objects, characteristics, and advantages of the present invention will be more apparent with reference to the following detailed description and the accompanying drawings.

BRIEF DESCRIPTION OF DRAWINGS

FIG. 4 is a diagram illustrating the respective components in a monitoring information table and a sensor unit information table stored in the respective units in the object monitoring system according to the embodiment.

DESCRIPTION OF EMBODIMENTS

Figure 1:
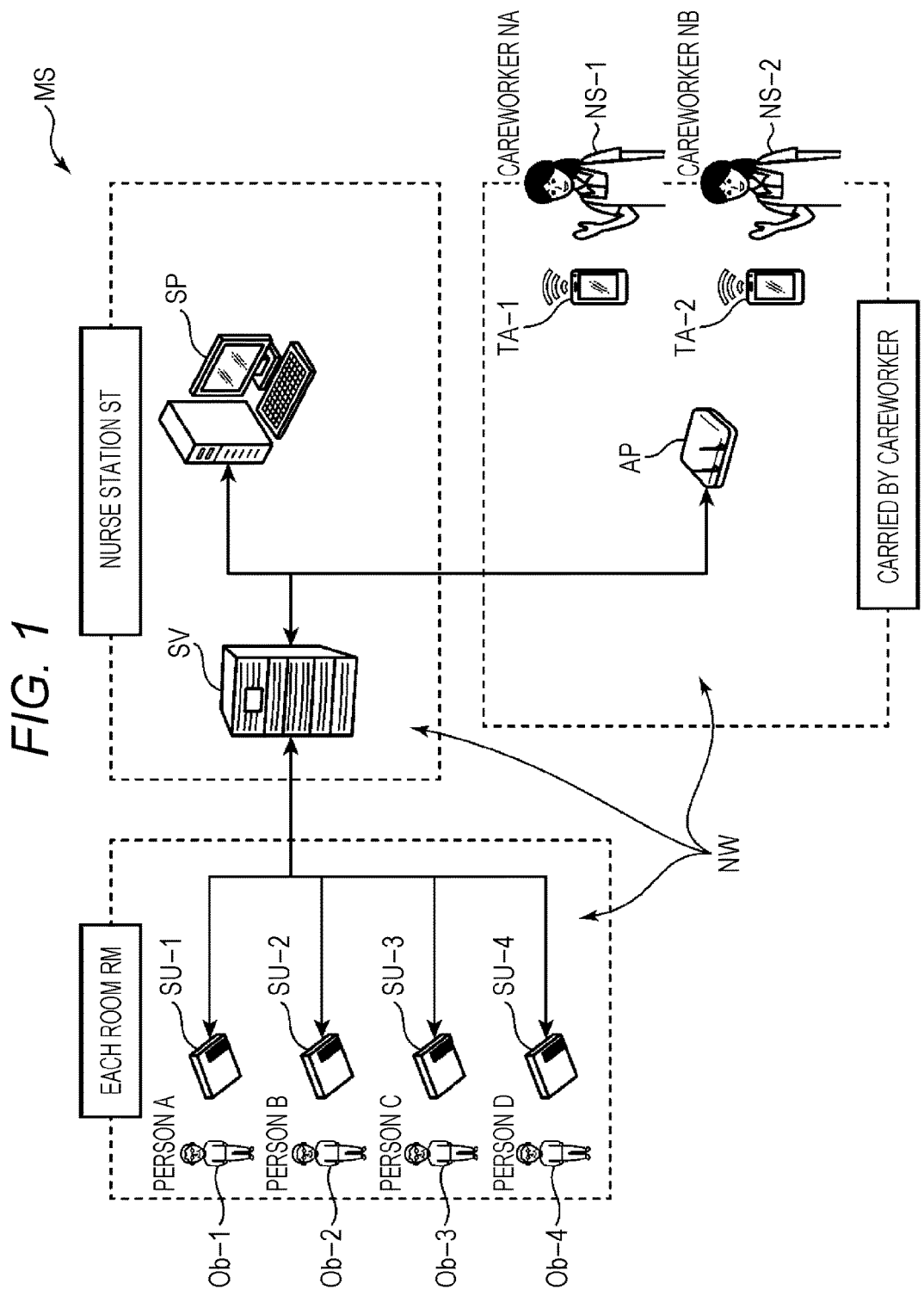
FIG. 1 is a diagram illustrating a configuration of an object monitoring system according to an embodiment.

One embodiment of the present invention will be described below with reference to the drawings. The components denoted with the same reference numerals in the drawings indicate the same components, and the description thereof will be omitted as needed. In the specification, components are denoted with a reference numeral without a subscript when collectively denoted, and an individual component is denoted with a reference numeral with a subscript.

The object monitoring system is directed for sensing an object to be monitored (to be watched) Ob and monitoring the object Ob by a plurality of devices. A central processing apparatus for the object monitoring system is directed for managing monitoring information on the object, and when receiving a condition checking notification communication signal for notifying that a condition of the object based on the monitoring information is being checked in a condition check mode of checking a condition of the object from a terminal apparatus among a plurality of terminal apparatuses, transmitting a condition check function prohibiting command communication signal for giving notification of a command to prohibit executing the condition check mode based on the monitoring information to the other terminal apparatuses except the terminal apparatus among the terminal apparatuses. Preferably, the central processing apparatus for the object monitoring system is directed for transmitting a condition check function canceling command communication signal for giving notification of a command to cancel the prohibition of executing the condition check mode based on the monitoring information to the other terminal apparatuses when receiving a condition check cancel notification communication signal for giving notification of the end of the condition check mode from the terminal apparatus before receiving an action notification communication signal for notifying that an intention to actually perform an action on the object based on the monitoring information is received from any of the terminal apparatuses. A terminal apparatus for the object monitoring system has a plurality of operation modes including a condition check mode of checking a condition of the object until receiving an intention to actually perform an action on the object based on the monitoring information after receiving the monitoring information, and prohibits executing the condition check mode on the object based on the received monitoring information while other terminal apparatus is checking the condition of the object based on the received monitoring information in the condition check mode. Before one terminal apparatus or other terminal apparatus receives an intention to actually perform an action on the object based on the monitoring information, when the other terminal apparatus ends the condition check of the object based on the received monitoring information, the terminal apparatus for the object monitoring system preferably cancels the prohibition of executing the condition check mode on the object based on the received monitoring information. The terminal apparatus for the object monitoring system preferably displays checking information indicating that other terminal apparatus is checking a condition of the object based on the received monitoring information while the other terminal apparatus is checking the condition of the object based on the received monitoring information in the condition check mode. Preferably, the terminal apparatus for the object monitoring system erases the screen displaying the monitoring information thereon when the other terminal apparatus receives an intention to actually perform an action on the object based on the monitoring information. Preferably, the terminal apparatus for the object monitoring system forcibly ends the condition check mode in execution when the other terminal apparatus receives an intention to actually perform an action on the object based on the received monitoring information while the condition of the object based on the received monitoring information is being checked in the condition check mode.

Figure 2:
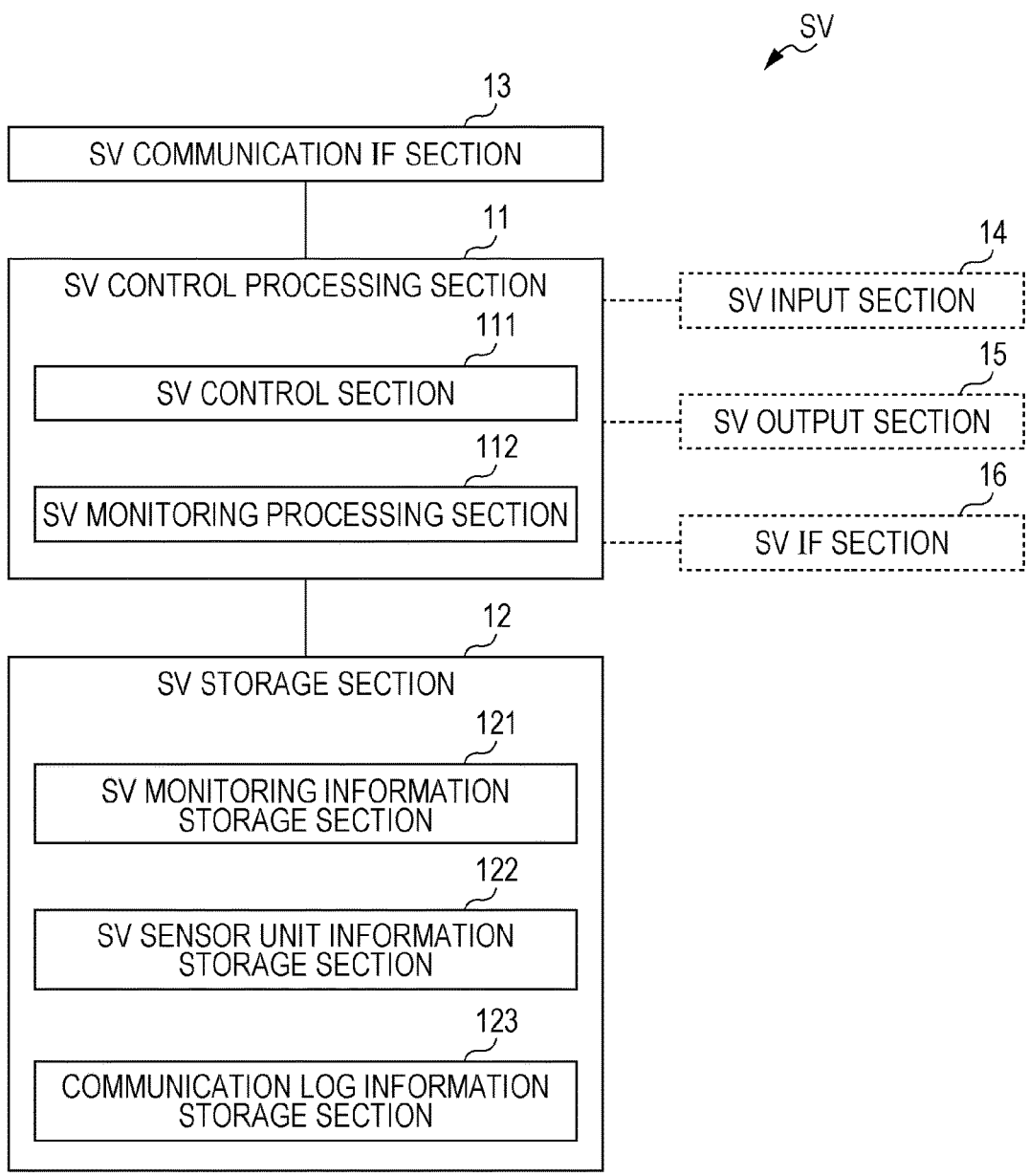
FIG. 2 is a diagram illustrating a configuration of a management server unit in the object monitoring system according to the embodiment.
Figure 3:
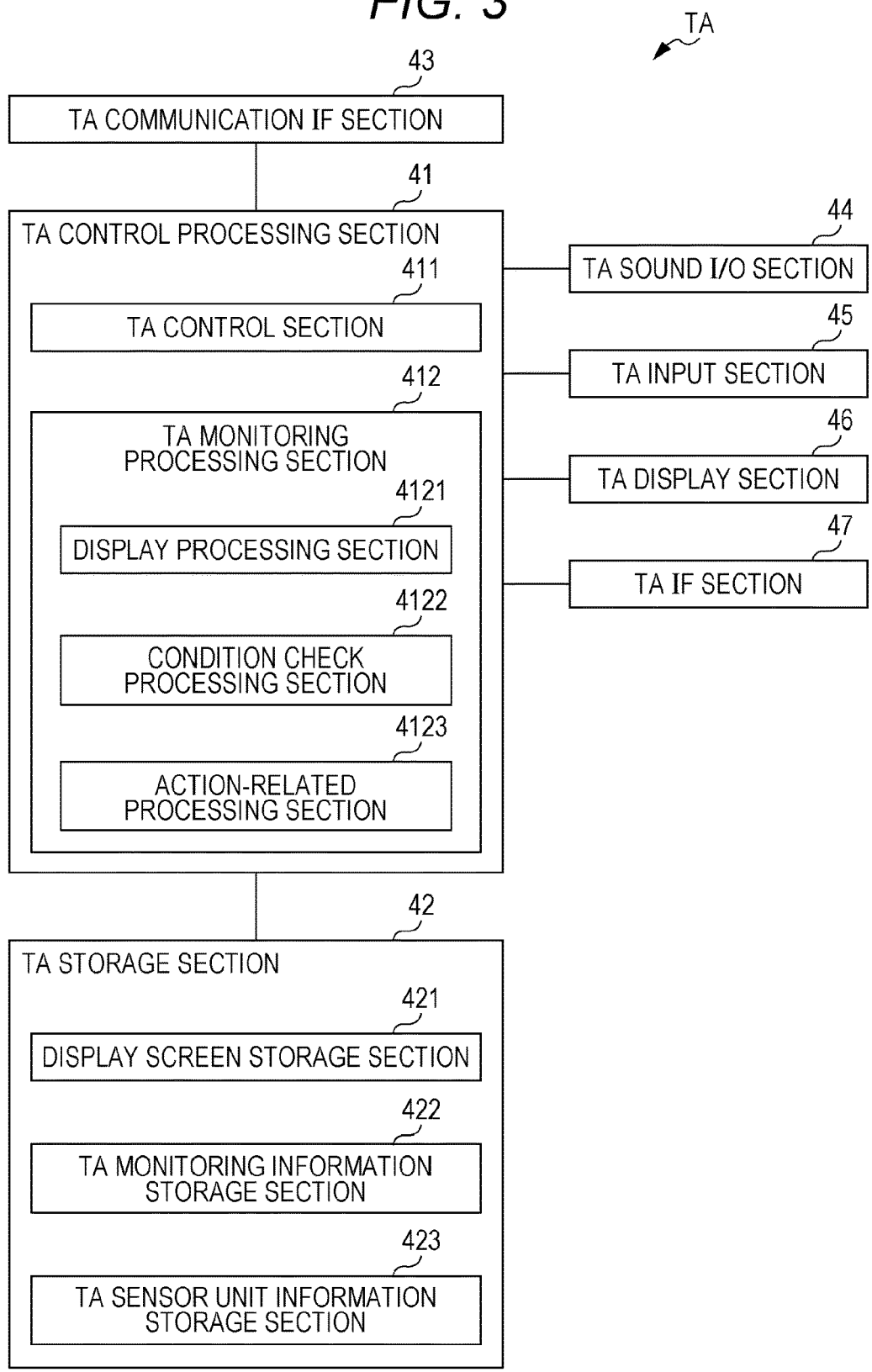
FIG. 3 is a diagram illustrating a configuration of a portable terminal unit in the object monitoring system according to the embodiment.

FIG. 1 is a diagram illustrating a configuration of the object monitoring system according to the embodiment. FIG. 2 is a diagram illustrating a configuration of a management server unit in the object monitoring system according to the embodiment. FIG. 3 is a diagram illustrating a configuration of a portable terminal unit in the object monitoring system according to the embodiment. FIG. 4 is a diagram illustrating the respective components in a monitoring information table and a sensor unit information table stored in the respective units in the object monitoring system according to the embodiment. FIG. 4A illustrates the monitoring information table, and FIG. 4B illustrates the sensor unit information table.

The object monitoring system MS includes one or more sensor units SU (SU-1 to SU-4), a management server unit SV, a fixed terminal unit SP, and one or more portable terminal units TA (TA-1, TA-2) as illustrated in FIG. 1, for example, and the components are communicably connected via a network (communication line) NW such as local area network (LAN), telephone line network or data communication network in a wired or wireless manner. The network NW may be provided with a relay device such as repeater, bridge, router, or cross-connect for relaying a communication signal. In the example illustrated in FIG. 1, the sensor units SU-1 to SU-4, the management server unit SV, the fixed terminal unit SP, and the portable terminal units TA-1, TA-2 are communicably connected to each other via the wireless LAN (such as LAN in the IEEE802.11 standard) NW including an access point AP.

The object monitoring system MS is installed at an appropriate place depending on an object Ob. The object (person to be watched) Ob is a person in need of nursing due to illness or injury, a person in need of care due to reduced physical performance, a person living alone, or the like. In particular, it is preferable that the object Ob needs to be found when a predetermined uncomfortable event such as abnormal condition occurs to him/her in terms of possible early discovery and early action. Thus, the object monitoring system MS is preferably installed in a building such as hospital, nursing facility for the aged, or house depending on the type of the object Ob. In the example illustrated in FIG. 1, the object monitoring system MS is installed in a nursing facility building provided with a plurality of rooms RM in which a plurality of objects Ob stay and a plurality of rooms such as nurse station ST.

The sensor unit SU is a device including a communication function of making communication with the other units SV, SP, and TA via the network NW and directed for shooting an object Ob, generating an image, and sensing the object Ob from the generated image. More specifically, the sensor unit SU is configured of a communication interface circuit (such as LAN card) for making communication with the other units SV, SP and TA via the network, for example, a Doppler-shift body motion sensor for sensing an object Ob by exchanging a microwave and detecting Doppler shift of the microwave caused by a body motion (such as breathing) of the object Ob, an image sensor for shooting the object Ob and generating an image, a data processing circuit for determining a state (condition) of the object Ob as the sensing result of the object Ob on the basis of output of the body motion sensor (body motion sensor output) and output (image) of the image sensor, and a control circuit and its peripheral circuit for controlling them, and transmits the sensing result to the management server unit SV. The sensor unit SU transmits the generated image (including still image and animation) to the other predetermined units SV, SP, and TA. Further, according to the present embodiment, the sensor unit SU includes a nurse call circuit for notifying the fixed terminal unit SP or the portable terminal units TA of a nurse call, and a call circuit for making audio call with the fixed terminal unit SP or the portable terminal units TA, and can make a nurse call or audio call. FIG. 1 illustrates the first to fourth sensor units SU-1 to SU-4 by way of example, where the first sensor unit SU-1 is installed in a room RM-1 (not illustrated) of the person A Ob-1 as one of the objects Ob, the second sensor unit SU-2 is installed in a room RM-2 (not illustrated) of the person B Ob-2 as one of the objects Ob, the third sensor unit SU-3 is installed in a room RM-3 of the person C Ob-3 as one of the objects Ob, and the fourth sensor unit SU-4 is installed in a room RM-4 (not illustrated) of the person D Ob-4 as one of the objects Ob.

The fixed terminal unit SP includes a communication function of making communication with the other units SU, SV, and TA via the network NW, a display function of displaying predetermined information, and an input function of inputting predetermined commands or data, and functions as a user interface (UI) of the object monitoring system MS by inputting a predetermined command or data to be given to the management server unit SV or the portable terminal units TA or displaying a sensing result or image acquired by the sensor units SU. The fixed terminal unit SP can be configured of a computer with a communication function, for example.

The management server unit SV includes a communication function of making communication with the other units SU, SP, and TA via the network NW, and is directed for receiving the sensing result on an object Ob from a sensor unit SU and managing the monitoring information on the monitoring of the object Ob. The management server unit SV includes a server control processing section (SV control processing section) 11, a server storage section (SV storage section) 12, and a server communication interface section (SV communication IF section) 13 as illustrated in FIG. 2, for example. The management server unit SV is an exemplary central processing apparatus.

The SV communication IF section 13 is a communication device connected to the SV control processing section 11 and directed for making communication under control of the SV control processing section 11. The SV communication IF section 13 generates a communication signal housing therein data input from the SV control processing section 11 and to be transferred according to a communication protocol used in the network NW of the object monitoring system MS, and transmits the generated communication signal to the other units SU, SP, and TA via the network NW. The SV communication IF section 13 receives a communication signal from other unit SU, SP, or TA via the network NW, extracts data from the received communication signal, converts the extracted data into data in a form processable by the SV control processing section 11, and outputs the converted data to the SV control processing section 11.

The SV storage section 12 is a circuit connected to the SV control processing section 11 and directed for storing various predetermined programs and various items of predetermined data under control of the SV control processing section 11. The predetermined programs include control processing programs such as a server program for providing a client with data in response to a request of the client (such as the fixed terminal unit SP or the portable terminal unit TA according to the present embodiment), and a monitoring processing program for processing the monitoring information on the monitoring of the objects Ob. The predetermined data includes items of data such as monitoring information on the monitoring of the objects Ob, sensor unit information on the sensor units SU, and communication log information on a communication history of communication signals. The SV storage section 12 includes a read only memory (ROM), electrically erasable programmable read only memory (EEPROM) as rewritable nonvolatile storage device, or the like, for example. The SV storage section 12 includes a random access memory (RAM) as a working memory of the SV control processing section 11 for storing data and the like caused while the predetermined programs are being executed.

The SV storage section 12 functionally includes a server monitoring information storage section (SV monitoring information storage section) 121 for storing the monitoring information therein, a server sensor unit information storage section (SV sensor unit information storage section) 122 for storing the sensor unit information therein, and a communication log information storage section 123 for storing the communication log information therein.

The SV monitoring information storage section 121 is directed for storing the monitoring information on the monitoring of the objects Ob. The monitoring information is information on the objects Ob received from the sensor units SU, the fixed terminal unit SP, and the portable terminal units TA, and includes a sensor unit identifier (sensor ID) for specifying and identifying a sensor unit SU, information (determination result information; including wake-up, rising, falling, or slight body motion abnormality according to the present embodiment) associated with the sensor ID and indicating a determination result determined as a state of an object Ob by the sensor unit SU having the sensor ID, information (determination time information) associated with the sensor ID and indicating a time when a state of an object Ob is determined by the sensor unit SU having the sensor ID, a still image (one image (such as the last image) if the determination is made by use of a plurality of images) of an object Ob associated with the sensor ID and used for determining a state of the object Ob by the sensor unit SU having the sensor ID, a communication address (such as IP address) associated with the sensor ID of the sensor unit SU having the sensor ID, condition checking information associated with the sensor ID and indicating whether a condition of an object Ob monitored by the sensor unit SU having the sensor ID is being checked by the portable terminal units TA, and action information associated with the sensor ID and indicating whether an intention to perform an action such as lifesaving, nursing, care, or help for an object Ob monitored by the sensor unit SU having the sensor ID is input into a portable terminal unit TA. A communication signal reception time when notification of the determination result and the image are given may be used instead of the determination time.

The monitoring information is stored in the SV monitoring information storage section 121 in a table form according to the present embodiment. A monitoring information table MT registering the monitoring information therein includes sensor ID field 4231 registering the sensor ID therein, determination result field 4232 registering therein the determination result information by a sensor unit SU corresponding to a sensor ID registered in sensor ID field, determination time field 4233 registering therein the determination time information for a sensor unit SU corresponding to a sensor ID registered in sensor ID field, still image field 4234 registering therein the still image by a sensor unit SU corresponding to a sensor ID registered in sensor ID field, animation field 4235 registering therein communication address (such as IP address) of a sensor unit SU corresponding to a sensor ID registered in sensor ID field, condition checking field 4236 registering therein the condition checking information on an object Ob monitored by a sensor unit SU corresponding to a sensor ID registered in sensor ID field, and action field 4237 registering therein the action information for an object Ob monitored by a sensor unit SU corresponding to a sensor ID registered in sensor ID field as illustrated in FIG. 4A, for example, and includes a record per reception of a monitoring information communication signal described later. Condition checking field 4236 registers therein, as the condition checking information indicating whether the condition is being checked, the portable terminal identifier of a portable terminal unit TA checking a condition of an object Ob when the condition of the object Ob is being checked, and a flag "0" indicating the fact that the condition is not being checked when the condition of the object Ob is not being checked. The portable terminal identifier (portable terminal ID) is an identifier for specifying and identifying a portable terminal unit TA. Action field 4237 registers therein a flag indicating the action information on the presence of an intention to perform the action. For example, according to the present embodiment, action field 4237 registers therein a flag "1" indicating that an intention to perform the action is input into a portable terminal unit TA or a flag "0" indicating that an intention to perform the action is not input into a portable terminal unit TA. By default, condition checking field 4236 registers therein a flag "0" indicating that the condition is not being checked, and action field 4237 registers therein a flag "0" indicating that an intention to perform the action is not input. Still image field 4234 may register therein image data of a still image, for example, and may register therein a file name of the image data of the still image, for example. In the example illustrated in FIG. 4A, for the first record, "SU-1," "wake-up," "06:32," "SP1," ". . . " (** is an integer), "0," and "0" are registered in sensor ID field 4231, determination result field 4232, determination time field 4233, still image field 4234, animation field 4235, condition checking field 4236, and action field 4237, respectively.

In the example illustrated in FIG. 4A, the monitoring information table MT includes animation field 4235, but a table indicating a correspondence between sensor ID and communication address of a sensor unit SU from which live animation is to be acquired may be prepared separately from the monitoring information table MT, and may be stored in the SV monitoring information storage section 121, and animation field 4235 may be omitted from the monitoring information table MT illustrated in FIG. 4A.

The SV sensor unit information storage section 122 is directed for storing the sensor unit information on the sensor units SU. The sensor unit information includes place where a sensor unit SU is installed, and the name of an object monitored by the sensor unit SU. The sensor unit information is stored in the sensor unit information storage section 423 in a table form according to the present embodiment. A sensor unit information table DT registering the sensor unit information therein includes sensor ID field 4241 registering sensor ID therein, installation place field 4242 associated with the sensor ID and registering therein a place where the sensor unit SU having the sensor ID is installed, and object name field 4243 associated with the sensor ID and registering the name of an object Ob monitored by the sensor unit SU having the sensor ID as illustrated in FIG. 4B, for example, and includes a record per sensor ID. In the example illustrated in FIG. 4B, for the first record, "SU-1," "101," and "Kkawa Mko" are registered in sensor ID field 4241, installation place field 4242, and object name field 4243, respectively.

The communication log information storage section 123 is directed for storing the communication log information on a communication history of communication signals. The communication log information includes reception time information indicating a time to receive a communication signal, communication signal type information indicating a type of the communication signal, transmission source information indicating a transmission source of the communication signal, transmission time information indicating a time to transmit a communication signal, communication signal type information indicating a type of the communication signal, and transmission destination information indicating a transmission destination of the communication signal. When a communication signal is received, the reception time information, the communication signal type information, and the transmission source information are associated with each other and are stored in the communication log information storage section 123, and when a communication signal is transmitted, the transmission time information, the communication signal type information, and the transmission destination information are associated with each other and are stored in the communication log information storage section 123.

The SV control processing section 11 is a circuit for controlling each unit in the management server unit SV depending on the function of the unit, receiving the sensing result on an object Ob from a sensor unit SU, and managing the monitoring information on the object Ob. The SV control processing section 11 is configured of a central processing unit (CPU) and its peripheral circuits, for example. The SV control processing section 11 functionally includes a server control section (SV control section) 111 and a server monitoring processing section (SV monitoring processing section) 112 when the control processing programs are executed.

The SV control section 111 is directed for controlling each unit in the management server unit SV depending on the function of the unit, and controlling the entire management server unit SV.

The SV monitoring processing section 112 is directed for managing the monitoring information. More specifically, for example, when the SV communication IF section 13 receives a monitoring information communication signal described below from a sensor unit SU, the SV monitoring processing section 112 registers each item of information housed in the received monitoring information communication signal in the monitoring information table MT and stores it in the SV monitoring information storage section 121, and corrects the monitoring information communication signal as needed as described below and transmits the corrected monitoring information communication signal to the fixed terminal unit SP and each portable terminal unit from the SV communication IF section 13 according to the present embodiment. When the SV communication IF section 13 receives a condition checking notification communication signal for notifying that a condition of the object Ob based on the monitoring information is being checked from a portable terminal unit TA among the portable terminal units TA, the SV monitoring processing section 112 transmits a condition check function prohibiting command communication signal for notifying the other portable terminal units TA except the portable terminal unit TA among the portable terminal units TA and the fixed terminal unit SP of a command to prohibit checking a condition of the object Ob based on the monitoring information by the SV communication IF section 13. When the SV communication IF section 13 receives a condition check cancel notification communication signal for giving notification of the end of the condition check from the portable terminal unit TA before the SV communication IF section 13 receives an action notification communication signal for notifying that an intention to actually perform an action on the object Ob based on the monitoring information is received from any of the portable terminal units TA, the SV monitoring processing section 112 transmits a condition check function canceling command communication signal for notifying the other portable terminal units TA and the fixed terminal unit SP of a command to cancel the prohibition based on the monitoring information by the SV communication IF section 13. When the SV communication IF section 13 receives the action notification communication signal from any of the portable terminal units TA, the SV monitoring processing section 112 transmits a no-action notification communication signal for notifying that the actual action for the object Ob based on the monitoring information is not required to the other portable terminal units TA and the fixed terminal unit SP by the SV communication IF section 13. When exchanging each communication signal described above, the SV monitoring processing section 112 then stores each item of communication log information on each communication signal in the communication log information storage section 123. When exchanging each communication signal, the SV monitoring processing section 112 rewrites and updates condition checking field 4236 or action field 4237 in the monitoring information table MT as needed.

As illustrated in broken lines in FIG. 2, the management server unit SV may further include a server input section (SV input section) 14 connected to the SV control processing section 11 and directed for inputting various commands or various items of data, for example, a server output section (SV output section) 15 for outputting various commands or various items of data input by the SV input section 14, and information on the monitoring of the objects Ob, and a server interface section (SV IF section) 16 for inputting and outputting data into and from an external device as needed.

The management server unit SV can be configured of a computer with a communication function, for example.

The portable terminal unit TA will be described below. The portable terminal unit TA includes a communication function of making communication with the other units SV, SP, and SU via the network NW, a display function of displaying predetermined information, an input function of inputting predetermined commands or data, and a call function of making audio call, and is directed for receiving and displaying the monitoring information on the monitoring of the objects Ob by inputting a predetermined command or data given to the management server unit SV or the sensor units SU or displaying the sensing results or images obtained by the sensor units SU in response to a notification from the management server unit SV. The portable terminal unit TA is an exemplary terminal apparatus.

The portable terminal unit TA includes a terminal control processing section (TA control processing section) 41, a terminal storage section (TA storage section) 42, a terminal communication interface section (TA communication IF section) 43, a terminal sound I/O section (TA sound I/O section) 44, a terminal input section (TA input section) 45, a terminal display section (TA display section) 46, and a terminal interface section (TA IF section) 47 according to the present embodiment as illustrated in FIG. 3, for example.

The TA sound I/O section 44 is a device connected to the TA control processing section 41 and directed for acquiring and inputting external sound into the portable terminal unit TA and generating and outputting sound depending on an electric signal indicating the sound under control of the TA control processing section 41. The TA sound I/O section 44 is configured of a microphone for converting sound acoustic vibration into an electric signal, and a speaker for converting a sound electric signal into sound acoustic vibration. The TA sound I/O section 44 outputs an electric signal indicating external sound to the TA control processing section 44, and converts and outputs an electric signal input from the TA control processing section 44 into sound acoustic vibration.

The TA input section 45 is a device connected to the TA control processing section 41 and directed for receiving and inputting a predetermined operation into the portable terminal unit TA, for example, which is a plurality of input switches assigned with predetermined functions, for example. The predetermined operations include various operations required for monitoring an ID input operation for log-in or an input operation as to whether to perform the action such as nursing on an object Ob notified of the sensing result and the image. The TA display section 46 is a device connected to the TA control processing section 41 and directed for displaying predetermined operation contents input from the TA input section 45 and the monitoring information (such as states or images of the objects Ob determined) on the monitoring of the objects Ob monitored by the object monitoring system MS under control of the TA control processing section 41, which is a display device such as LCD or organic EL display. According to the present embodiment, a touch panel is configured of the TA input section 45 and the TA display section 46. In this case, the TA input section 45 is a resistive-system or capacitance-system position input device for detecting and inputting an operation position, for example. In the touch panel, the position input device is provided on the display surface of the TA display section 46, one or more candidates of input contents capable of being input are displayed on the TA display section 46, and when the user (monitoring person) such as nurse or careworker contacts a display position of his/her desired input contents, the position is detected by the position input device and the display contents displayed at the detected position are input as user operation input contents into the portable terminal unit TA.

The TA IF section 47 is a device connected to the TA control processing section 41 and directed for inputting and outputting data into and from an external device under control of the TA control processing section 41, which is an interface circuit in Bluetooth (registered trademark) standard, an interface circuit for making infrared communication in infrared data association (IrDA) standard, or an interface circuit using universal serial bus (USB) standard, for example.

The TA communication IF section 43 is a device connected to the TA control processing section 41 and directed for making communication under control of the TA control processing section 41 similarly to the SV communication IF section 13. The TA communication IF section 43 generates a communication signal housing data input from the TA control processing section 41 and to be transferred according to a communication protocol used in the network NW of the object monitoring system MS, and transmits the generated communication signal to the other units SU, SV, and SP via the network NW. The TA communication IF section 43 receives a communication signal from other unit SU, SV or SP via the network NW, extracts data from the received communication signal, and converts the extracted data into data in a form processable by the TA control processing section 41, and outputs the converted data to the TA control processing section 41.

The TA storage section 42 is a circuit connected to the TA control processing section 41 and directed for storing various predetermined programs and various items of predetermined data under control of the TA control processing section 41 similarly to the SV storage section 12. The predetermined programs include control processing programs such as monitoring processing programs for processing the monitoring information on the monitoring of the objects Ob. The monitoring processing programs include a display processing program of processing the operation of displaying the monitoring information, a condition check processing program of processing the operation of checking conditions of the objects Ob, and an action-related processing program of processing the operation of performing the action such as nursing on an object Ob. The predetermined data includes the monitoring information on the monitoring of the objects Ob, and the sensor unit information on the sensor units SU. The TA storage section 42 includes a ROM or EEPROM, for example. The TA storage section 42 includes a RAM as working memory for the TA control processing section 41, which is for storing data caused in executing the predetermined programs. The TA storage section 42 functionally includes a display screen storage section 421, a terminal monitoring information storage section (TA monitoring information storage section) 422, and a terminal sensor unit information storage section (TA sensor unit information storage) 423.

The display screen storage section 421 is directed for storing an image to be displayed on the TA display section 46 under control of a display processing section 4121 described below in the TA control processing section 41, which is a VRAM (video memory), for example. A plane size stored in the display screen storage section 421 is typically the same as the size of the screen display region of the TA display section 46, but when a plurality of monitoring information communication signals are received, the monitoring information screen displaying the monitoring information housed in one monitoring information communication signal is formed in the typical plane size, and a plurality of monitoring information screens corresponding to the monitoring information communication signals are coupled with each other in time series to be formed in plane, and thus the plane size when the monitoring information communication signals are received accords to the number of monitoring information screens. Only the part in the size of the screen display region of the TA display section 46 among the monitoring information screens formed in plane is displayed on the TA display section 46 by the display processing section 4121 in response to an input operation received by the TA input section 45.

The TA monitoring information storage section 422 is directed for storing the monitoring information on the monitoring of the objects Ob. The TA monitoring information storage section 422 registers the monitoring information in the monitoring information table MT described above with reference to FIG. 4A thereby to store the monitoring information similarly to the SV monitoring information storage section 121.

The TA sensor unit information storage section 423 is directed for storing the sensor unit information on the sensor units SU. The TA sensor unit information storage section 423 registers the sensor unit information in the sensor unit information table DT described above with reference to FIG. 4B and stores the sensor unit information similarly to the SV sensor unit information storage section 122.

The TA control processing section 41 is a circuit for controlling each unit in the portable terminal unit TA depending on the function of the unit, and processing the monitoring information on the monitoring of the objects Ob in a plurality of operation modes including a condition check mode of checking conditions of the objects Ob. The TA control processing section 41 is configured of a CPU and its peripheral circuits, for example, similarly to the SV control processing section 11. The TA control processing section 41 functionally includes a terminal control section (TA control section) 411 and a terminal monitoring processing section (TA monitoring processing section) 412 when the control progressing program is executed, and the TA monitoring processing section 412 functionally includes the display processing section 4121, a condition check processing section 4122, and an action-related processing section 4123.

The TA control section 411 controls each unit in the portable terminal unit TA depending on the function of the unit, and controls the entire portable terminal unit TA.

The TA monitoring processing section 412 is directed for processing the monitoring information on the monitoring of the objects Ob. More specifically, when the TA communication IF section 43 receives the monitoring information communication signal, the TA monitoring processing section 412 registers the monitoring information on an object Ob housed in the received monitoring information communication signal in the monitoring information table MT, and stores the monitoring information in the TA monitoring information storage section 422.

The display processing section 4121 is directed for processing the operation of displaying the monitoring information. More specifically, when the TA communication IF section 43 receives the monitoring information communication signal, for example, the display processing section 4121 forms a monitoring information screen 52 for displaying the monitoring information on the object Ob housed in the received monitoring information communication signal thereon in the display screen storage section 421, and displays it on the TA display section 46. When the TA communication IF section 43 receives the condition check function prohibiting command communication signal, the display processing section 4121 displays checking information indicating that other portable terminal unit TA is checking the condition of the object Ob designated by the received condition check function prohibiting command communication signal on the TA display section 46. The checking information is displayed in a condition checking main region 541 in a condition checking screen 54 of the other unit as described below, for example (see FIG. 12 described below).

The condition check processing section 4122 is directed for processing the operation of checking a condition of the object Ob. More specifically, when the TA communication IF section 43 receives the condition check function prohibiting command communication signal, for example, the condition check processing section 4122 prohibits the operation of checking a condition of the object Ob designated in the received condition check function prohibiting command communication signal. When the TA communication IF section 43 receives the condition check function canceling command communication signal for giving notification of a command to cancel the prohibition commanded in the received condition check function prohibiting command communication signal before the TA communication IF section 43 receives an intention to actually perform an action on the object Ob designated in the received condition check function prohibiting command communication signal from the TA input section 45 in the portable terminal unit TA or receives the no-action notification communication signal for notifying that an intention to actually perform an action on the object Ob designated in the received condition check function prohibiting command communication signal is received by other portable terminal unit TA, the condition check processing section 4122 cancels the prohibition commanded in the received condition check function prohibiting command communication signal. When the TA communication IF section 43 receives the condition check function canceling command communication signal, the display processing section 4121 displays the monitoring information in a condition checkable state on the TA display section 46. When receiving an input operation of checking a condition of an object Ob such as an input operation on the "talk" button 525 or an input operation on the "view LIVE" button 526, the condition check processing section 4122 transmits a condition checking notification communication signal for notifying that the condition of the object Ob is being checked to the management server unit SV by the TA communication IF section 43. When finishing checking the condition of the object Ob, the condition check processing section 4122 transmits a condition check cancel notification communication signal for giving notification of the end of the condition check to the management server unit SV by the TA communication IF section 43. When exchanging each communication signal, the condition check processing section 4122 rewrites and updates condition checking field 4236 or action field 4237 in the monitoring information table MT as needed.

The action-related processing section 4123 is directed for processing the operation for the action such as nursing on an object Ob. More specifically, when receiving an input operation of inputting an intention to actually perform an action on an object Ob, such as an input operation on the "action" button 524 described below, the action-related processing section 4123 transmits an action notification communication signal for notifying that the intention to actually perform an action on the object Ob is received to the management server unit SV by the TA communication IF section 43. If an object Ob whose condition is being checked is designated in a no-action notification communication signal when the condition check processing section 4122 is performing the operation of checking the condition of the object Ob and when the TA communication IF section 43 receives the no-action notification communication signal, the action-related processing section 4123 forcibly ends the operation of the condition check processing section 4122 in execution. When transmitting the action notification communication signal, the action-related processing section 4123 deletes (erases) the monitoring information screen with the sensor ID housed in the action notification communication signal from the display screen storage section 421. When receiving the no-action notification communication signal, the action-related processing section 4123 deletes (erases) the monitoring information screen with the sensor ID housed in the no-action notification communication signal from the display screen storage section 421. When exchanging each communication signal, the action-related processing section 4123 rewrites and updates condition checking field 4236 or action field 4237 in the monitoring information table MT as needed.

The portable terminal unit TA can be configured of a portable communication terminal apparatus such as tablet-type computer, Smartphone, or cell phone.

The operations according to the present embodiment will be described below. In the thus-configured object monitoring system MS, when powered on, each unit SU, SV, SP or TA initializes each section as needed and starts operating it. The control processing program is executed in the management server unit SV so that the SV control section 111 and the SV monitoring processing section 112 are functionally configured in the SV control processing section 11, and the control processing program is executed in the portable terminal unit TA so that the TA control section 411 and the TA monitoring processing section 412 are functionally configured in the TA control processing section 41 and the display processing section 4121, the condition check processing section 4122 and the action-related processing section 4123 are functionally configured in the TA monitoring processing section 412.

The thus-configured object monitoring system MS generally monitors each object Ob in the following operations. The sensor unit SU samples output of the body motion sensor and output of the image sensor at a predetermined sampling cycle, determines a state (condition) of the object Ob on the basis of the sampled output of the body motion sensor and the sampled output of the image sensor, and as a result of the determination, when determining that the object Ob is in a preset state (such as wake-up, rising, falling, or slight body motion abnormality according to the present embodiment), transmits, to the management server unit SV via the network NW, a communication signal (monitoring information communication signal) housing therein sensor ID of the unit, determination result information indicating the determination result determined as the state of the object Ob, time determination information indicating the determination time, image data of a still image (one image (such as the last image) when the determination is made by a plurality of images) of the object Ob used for the determination, communication address (such as IP address) of the unit as communication destination in which animation is downloaded, and the like. The communication address of the unit may be also used as the communication address of the transmission source housed in the header. The sensor unit SU can determine a state (condition) of an object Ob in a well-known technique. For example, when the body motion sensor detects a body motion of the chest (vertical motion of the chest) along with the breathing operation of the object Ob and detects disturbance of the cycle in the body motion of the chest or an amplitude in the body motion of the chest at a preset threshold or less, the sensor unit SU determines the fact as the slight body motion abnormality. For example, the sensor unit SU acquires an image of the object Ob by the image sensor, detects a person region of the object Ob from the acquired image, determines a posture (such as standing, sitting, or lying) of the object Ob on the basis of the aspect ratio of the detected person region, detects a position of the detected person region, and determines wake-up, rising, or falling on the basis of the detected posture and position of the object Ob.

When receiving the monitoring information communication signal from a sensor unit SU via the network NW, the management server unit SV registers the sensor ID, the determination result information, the determination time information, the image data of a still image, and the communication address for acquiring animation, which are housed in the monitoring information communication signal, in the monitoring information table MT thereby to mutually associate and store (record) them in the SV monitoring information storage section 121. When each item of the information is registered in the monitoring information table MT, the SV monitoring processing section 112 registers a default flag "0" in condition checking field 4236 and action field 4237. The management server unit SV then transmits the monitoring information communication signal to the fixed terminal unit SP and the portable terminal units TA in broadcast or multicast communication, for example. Thereby, notification of the state (condition) of the object Ob is given. When the communication address of the transmission source is used as the communication address for acquiring animation, the management server unit SV transfers a monitoring information communication signal so that the communication address of the transmission source serves as the communication address of the management server unit SV, and thus the management server unit SV houses the communication address of the sensor unit SU at the transmission source, which is housed in the header, in the payload of the monitoring information communication signal and then broadcasts the monitoring information communication signal. The management server unit SV may transmit the monitoring information communication signal to the portable terminal units TA previously associated with the sensor unit SU having transmitted the monitoring information communication signal in unicast.

When receiving the monitoring information communication signal from the management server unit SV via the network NW, the fixed terminal unit SP and the portable terminal units TA display the monitoring information on the monitoring of the object Ob housed in the monitoring information communication signal. The operation of displaying the monitoring information by the portable terminal unit TA will be described below in detail. With the operation, the object monitoring system MS generally senses each object Ob and monitors each object Ob by the sensor units SU, the management server unit SV, the fixed terminal unit SP, and the portable terminal units TA.

Figure 5:
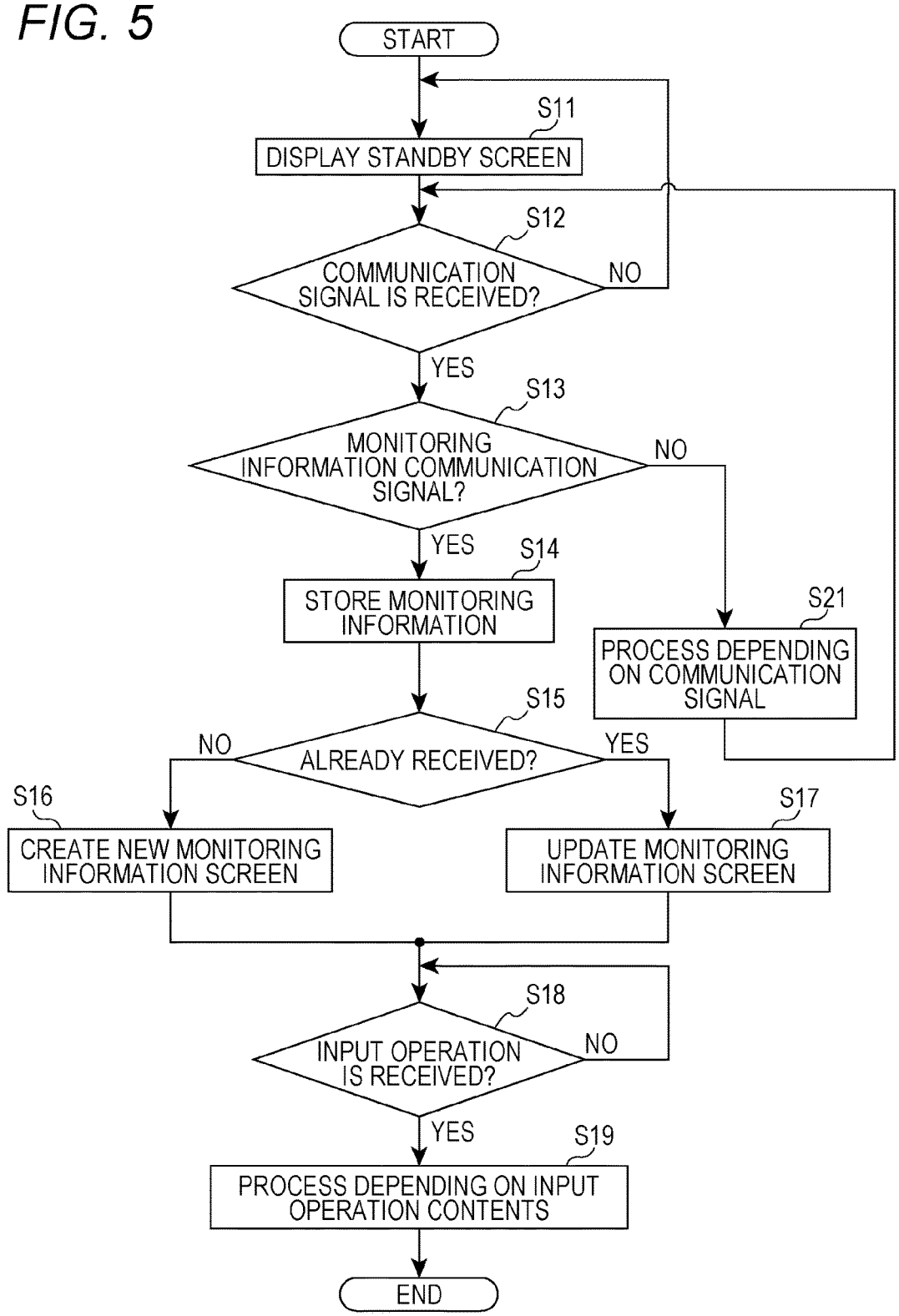
FIG. 5 is a flowchart illustrating the operations for giving notification of monitoring information in the portable terminal unit.
Figure 6:
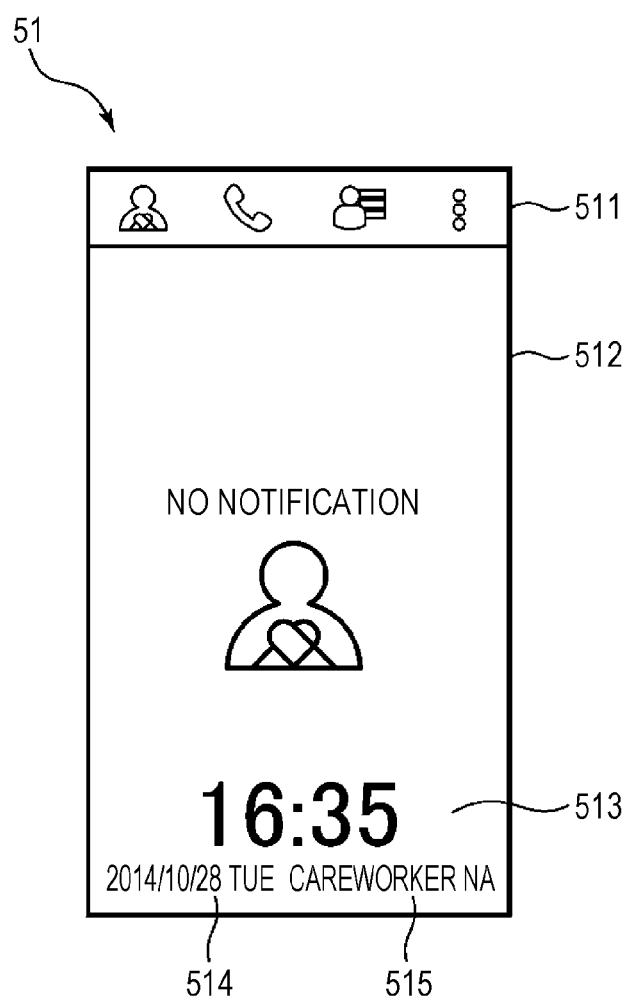
FIG. 6 is a diagram illustrating an exemplary standby display screen displayed on the portable terminal unit.
Figure 7:
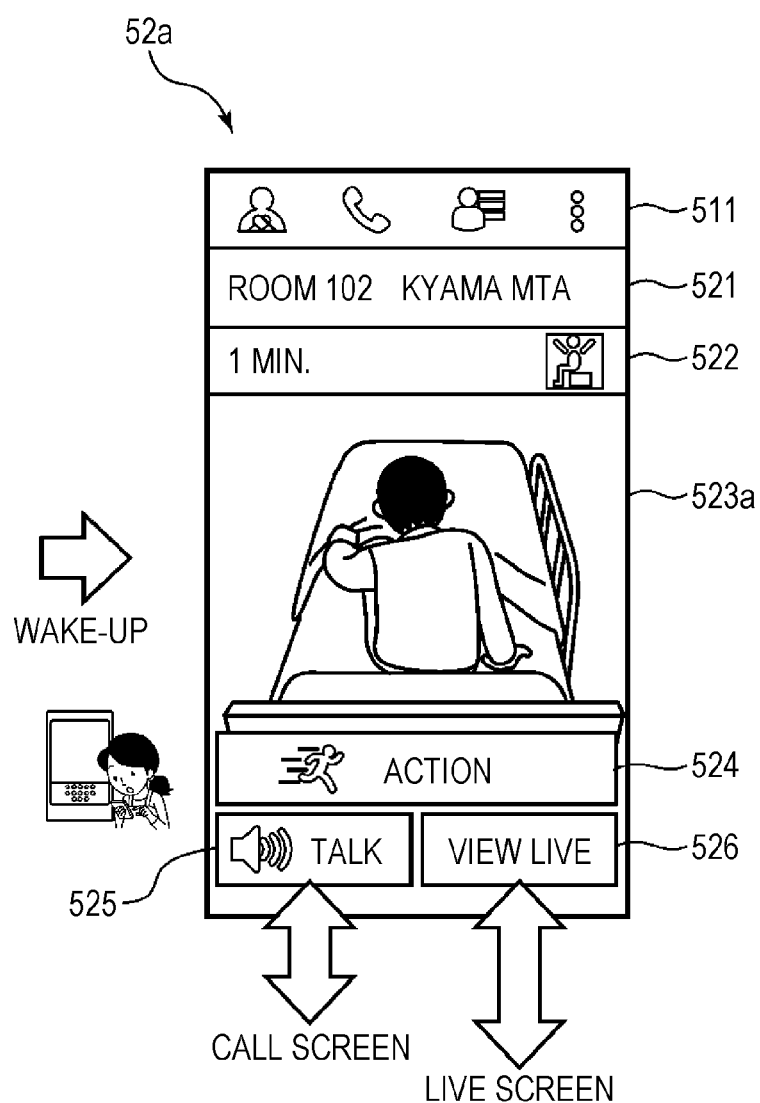
FIG. 7 is a diagram illustrating an exemplary monitoring information screen displayed on the portable terminal unit in response to a notification of wake-up of an object.
Figure 8:
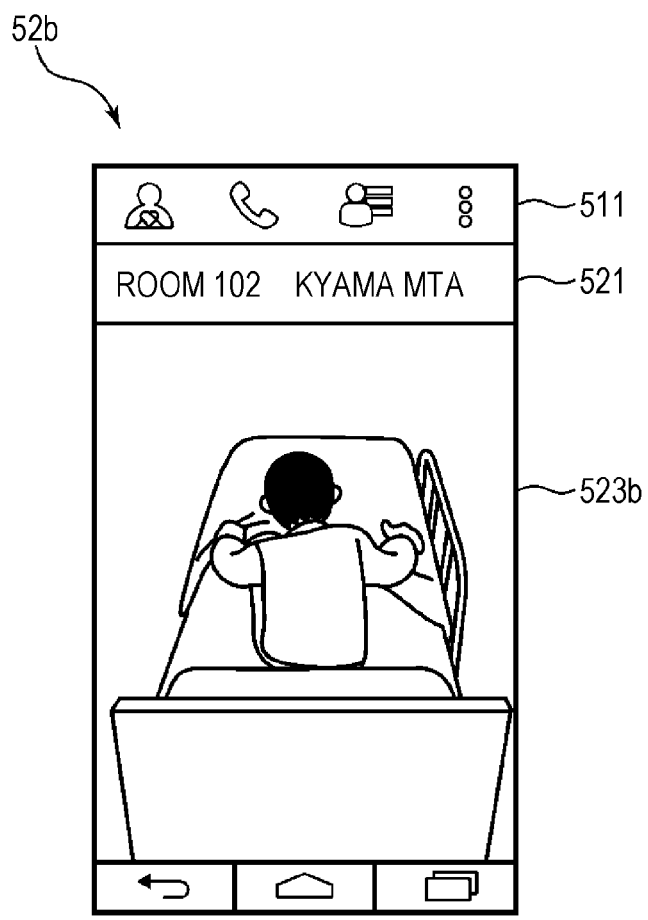
FIG. 8 is a diagram illustrating an exemplary monitoring information screen displayed in full-screen on the portable terminal unit.
Figure 9:
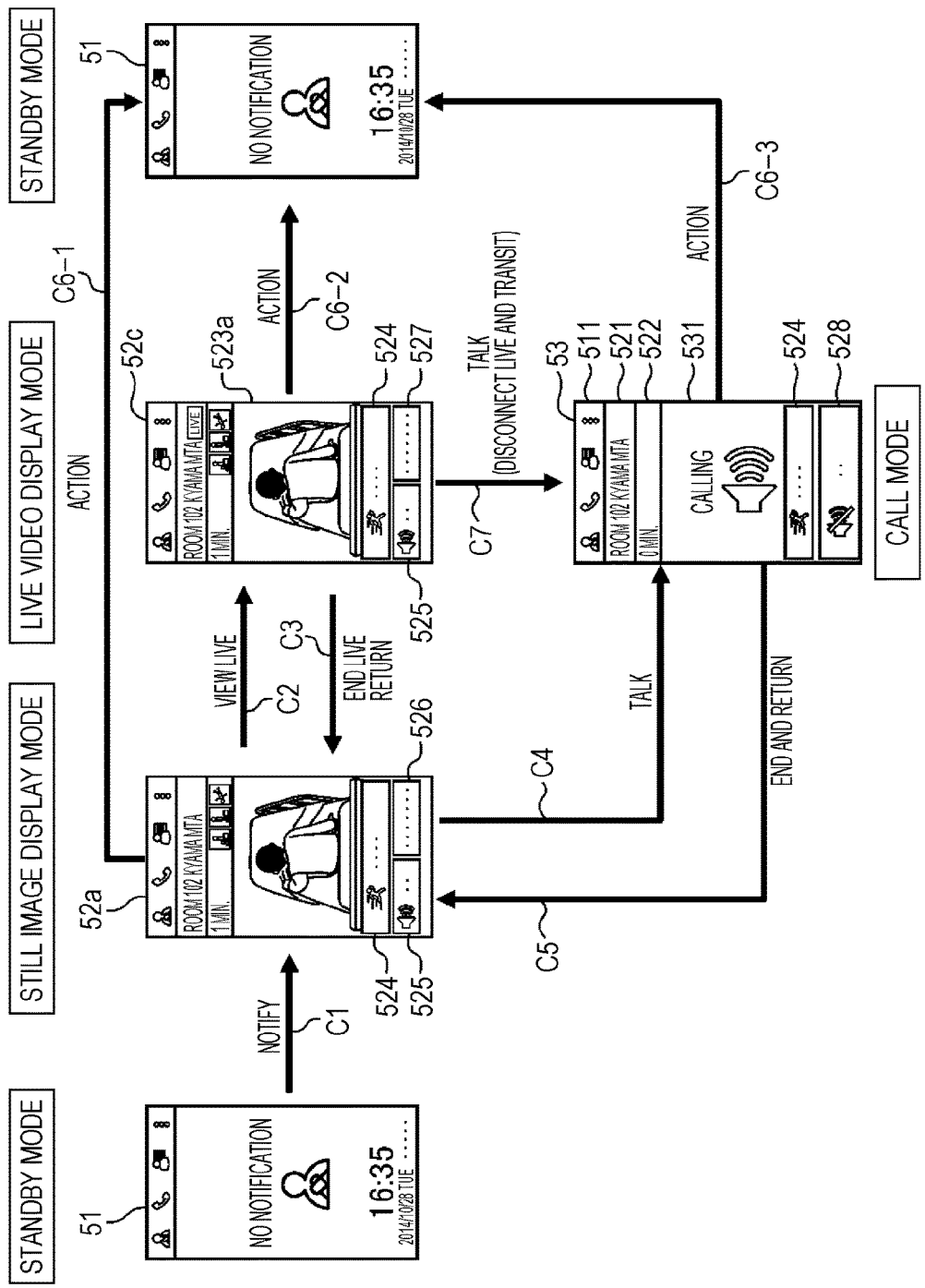
FIG. 9 is a diagram for explaining state transition on notification of monitoring information in the portable terminal unit.

The operation of displaying the monitoring information on the monitoring of the objects Ob, and its related operations in the object monitoring system MS will be described below. FIG. 5 is a flowchart illustrating the operations of giving notification of monitoring information in the portable terminal unit. FIG. 6 is a diagram illustrating an exemplary standby display screen displayed on the portable terminal unit. FIG. 7 is a diagram illustrating an exemplary monitoring information screen displayed on the portable terminal unit in response to a notification of wake-up of an object. FIG. 8 is a diagram illustrating an exemplary monitoring information screen displayed in full-screen on the portable terminal unit. FIG. 9 is a diagram for explaining state transition on notification of monitoring information in the portable terminal unit.

In FIG. 5, when the portable terminal unit TA is powered on and activated, and receives a log-in operation by a monitoring person (user) such as nurse or careworker, the TA monitoring processing section 412 displays the standby screen for waiting for a communication signal destined to the portable terminal unit TA on the TA display section 46 (S11). The standby screen 51 includes a menu bar region 511 for displaying a menu bar therein, a standby main region 512 for displaying a message (such as "no notification") indicating standby, and an icon therein, a time region 513 for displaying a current time therein, a year/month/day region 514 for displaying today's year/month/day, and a user name region 515 for displaying the name of a user currently logging in the portable terminal unit TA as illustrated in FIG. 6, for example.

The TA control section 411 in the portable terminal unit TA then determines whether the TA communication IF section 43 has received a communication signal (S12). As a result of the determination, when the communication signal has not been received (No), the portable terminal unit TA returns to the processing in S11, and as a result of the determination, when the communication signal has been received (Yes), the portable terminal unit TA performs the next processing in S13.

In the processing in S13, when the communication signal has been received, the TA monitoring processing section 412 in the portable terminal unit TA determines whether the received communication signal is a monitoring information communication signal. As a result of the determination, when the received communication signal is not a monitoring information communication signal (No), the TA control processing section 41 in the portable terminal unit TA performs an appropriate processing depending on the received communication signal (S21), and returns to the processing in S12. The appropriate processings depending on the received communication signal will be described below with reference to FIG. 11 by way of example. On the other hand, as a result of the determination, when the received communication signal is a monitoring information communication signal (Yes), the TA monitoring processing section 412 in the portable terminal unit TA registers the sensor ID, the determination result information, the determination time information, the image data of a still image, and the communication address for acquiring animation, which are housed in the received monitoring information communication signal, in the monitoring information table MT, mutually associates and registers them in the TA monitoring information storage section 422 (S14), and performs the processing in S15. When registering each item of the information in the monitoring information table MT, the TA monitoring processing section 412 registers a default flag "0" in condition checking field 4236 and action field 4237.

In the processing in S15, the display processing section 4121 in the portable terminal unit TA determines whether it has already received a monitoring information communication signal housing the same sensor ID as the sensor ID housed in the received monitoring information communication signal prior to the received monitoring information communication signal and whether the monitoring information screen for the previously-received monitoring information communication signal is created for display. More specifically, the display processing section 4121 determines whether the same sensor ID as the sensor ID housed in the received monitoring information communication signal is registered in sensor ID field 4231 in the record with a flag "0" registered in action field 4237, and then determines whether the monitoring information screen for the previously-received monitoring information communication signal is created for display. As a result of the determination, when the same sensor ID as the sensor ID housed in the received monitoring information communication signal is not registered in sensor ID field 4231 in the record with a flag "0" registered in action field 4237, it is determined that the monitoring information communication signal with the same sensor ID has not been received yet (No), and the portable terminal unit TA performs the processing in S16, on the other hand, as a result of the determination, when the same sensor ID as the sensor ID housed in the received monitoring information communication signal is registered in sensor ID field 4231 in the record with a flag "0" registered in action field 4237, it is determined that the monitoring information communication signal with the same sensor ID has been already received (Yes), and the portable terminal unit TA performs the processing in S17.

In the processing in S16, the display processing section 4121 in the portable terminal unit TA forms a new monitoring information screen depending on each item of information (each item of data) housed in the received monitoring information communication signal in the display screen storage section 421, and displays the formed monitoring information screen on the TA display section 46.

The monitoring information screen is directed for displaying the monitoring information on the monitoring of the objects Ob. The monitoring information screen 52 (52a) includes the menu bar region 511, an object name region 521 for displaying the installation place of a sensor unit SU with a sensor ID, and the name of an object Ob monitored by the sensor unit SU with the sensor ID, an icon region 522 for displaying an elapsed time from a determination time (or reception time) and an icon symbolically indicating a determination result, an image region 523a for displaying an image (still image, here) shot by the sensor unit SU with the sensor ID, the "action" button 524, the "talk" button 525, and the "view LIVE" button 526 as illustrated in FIG. 7, for example. The "action" button 524 is directed for inputting that the user of the portable terminal unit TA has an intention to perform the action such as nursing on the object Ob monitored by the sensor unit SU with the sensor ID in the portable terminal unit TA, and inputting a command to notify that the intention has been input to the fixed terminal unit SP and the other portable terminal units TA in the portable terminal unit. The "talk" button 525 is directed for inputting a command to communicably connect the sensor unit SU with the sensor ID and the portable terminal unit TA via the network NW. The "view LIVE" button 526 is directed for inputting a command to display an animation shot by the sensor unit SU with the sensor ID.

In order to create the monitoring information screen 52a according to each item of information housed in the received monitoring information communication signal, the display processing section 4121 searches the installation place and the object name corresponding to the sensor ID housed in the received monitoring information communication signal from the TA sensor unit information storage section 423 by use of the sensor ID as search key, finds an elapsed time from the determination time housed in the received monitoring information communication signal, and searches an icon corresponding to the determination result housed in the received monitoring information communication signal from the TA storage section 42 by use of the determination result as search key. Each icon corresponding to each determination result is previously stored in the TA storage section 42 in association with each determination result. The display processing section 4121 then displays a menu bar in the menu bar region 511, displays the searched installation place and object name in the object name region 521, displays the found elapsed time and the searched icon in the icon region 522, displays the image (still image) housed in the received monitoring information communication signal in the image region 523a, and displays the "action" button 524, the "talk" button 525, and the "view LIVE" button 526, thereby creating the monitoring information screen 52a. The display processing section 4121 then displays the newly-created monitoring information screen 52a on the TA display section 46.

The portable terminal unit TA may be configured such that when the TA control processing section 41 receives the input operation "tap" on the touch panel including the TA input section 45 and the TA display section 46, a monitoring information screen 52b with an image region 523b in full-screen instead of the image region 523a is displayed on the TA display section 46. The monitoring information screen 52b includes the menu bar region 511, the object name region 521, and the full-screen image region 523b for displaying an image (still image, here) shot by the sensor unit SU with the sensor ID in the entire region except the menu bar region 511 and the object name region 521 as illustrated in FIG. 8, for example. The full-screen display enables the monitoring person (user) to recognize how the object Ob is in more detail.

Returning to FIG. 5, in the processing in S17, the display processing section 4121 in the portable terminal unit TA updates the monitoring information screen 52a according to each item of information (each item of data) housed in the received monitoring information communication signal, and displays the updated monitoring information screen on the TA display section 46.

In order to update the monitoring information screen 52 according to each item of information housed in the received monitoring information communication signal, the display processing section 4121 finds an elapsed time from the determination time housed in the received monitoring information communication signal, and searches an icon corresponding to the determination result housed in the received monitoring information communication signal from the TA storage section 42 by use of the determination result as search key. The display processing section 4121 then displays the found elapsed time and the searched icon in the icon region 522 and displays the image (still image) housed in the received monitoring information communication signal in the image region 523a for the previously-displayed monitoring information screen 52, thereby updating the monitoring information screen 52. Here, the icon corresponding to the determination result housed in the previously-received monitoring information communication signal is displayed in the icon region 522, and thus the currently-searched icon is arranged in addition to the previously-displayed icon in time series and displayed in the icon region 522. For example, when notification of the determination result "wake-up" of an object Ob is given and then notification of the determination result "rising" is given, the icon indicating the determination result "rising" of the object Ob is arranged to the left of the icon indicating the determination result "wake-up" and displayed in the icon region 522 so that the monitoring information screen 52a, where the icon indicating the determination result "wake-up" of the object Ob is displayed in the icon region 522, illustrated in FIG. 7 is updated. The display processing section 4121 then displays the updated monitoring information screen 52a on the TA display section 46.

After the processing in S16 or after the processing in S17, the TA control processing section 41 in the portable terminal unit TA determines whether an input operation is received on the touch panel including the TA input section 45 and the TA display section 46 (S18). As a result of the determination, when an input operation is not received (No), the portable terminal unit TA returns to the processing in S18, on the other hand, as a result of the determination, when an input operation is received, the portable terminal unit TA performs the next processing in S19.

In the processing in S19, the TA control processing section 41 in the portable terminal unit TA performs an appropriate processing depending on the contents of the input operation, and ends the operation of displaying the monitoring information.

Exemplary appropriate processings depending on the contents of the input operation will be further described with reference to FIG. 9. The portable terminal unit TA has a plurality of operation modes including a condition check mode of checking a condition of the object Ob, and transits between modes in response to reception of a predetermined communication signal or reception of an input operation. More specifically, according to the present embodiment, the operation modes include a standby mode, a still image display mode, a LIVE video display mode, and a call mode, and each mode is taken in response to reception of a predetermined communication signal or reception of an input operation as illustrated in FIG. 9.

The standby mode is an operation mode of displaying the standby screen 51 on the TA display section 46, and corresponds to the processing in S11 to the processing in S13. When the TA communication IF section 43 receives a monitoring information communication signal in the standby mode, the standby mode transits to the still image display mode (C1).

The still image display mode is an operation mode of displaying the monitoring information screen 52a on the TA display section 46, and corresponds to the processing in S14 to the processing in S18. When an input operation on the "view LIVE" button 526 is received in the still image display mode, the still image display mode transits to the LIVE video display mode (C2). When an input operation on the "talk" button 525 is received, the still image display mode transits to the call mode (C4). When an input operation on the "action" button 524 is received, the still image display mode is kept if a monitoring information screen 52a is present in addition to the monitoring information screen 52a displayed on the TA display section 46, and the still image display mode transits to the standby mode when a monitoring information screen 52a is not present in addition to the monitoring information screen 52a displayed on the TA display section 46 (C6-1).

The LIVE video display mode is an operation mode of displaying an animation shot by a sensor unit SU on the TA display section 46, and corresponds to an exemplary condition check mode. In the processing in S18, when receiving an input operation on the "view LIVE" button 526, the TA control processing section 41 in the portable terminal unit TA transits to the LIVE video display mode, and as an example of the processing in S19, the portable terminal unit TA is connected to the sensor unit SU monitoring the object Ob currently displayed on the TA display section 46 by the display processing section 4121 and the condition check processing section 4122 in the TA monitoring processing section 412 to be able to download an animation via the network NW, and the animation of the object Ob is streamed in the image region 523a on a monitoring information screen 52c (or the image region 523b switched by "tap"), for example (C2). The monitoring information screen 52c displaying the LIVE video thereon is provided with an "end LIVE" button 527 instead of the "view LIVE" button 526.

The "end LIVE" button 527 is directed for inputting a command to end the LIVE video display mode. The condition check processing section 4122 in the portable terminal unit TA then transmits a condition checking notification communication signal for notifying that the condition of the object Ob is being checked to the management server unit SV. The condition checking notification communication signal houses therein condition checking information indicating that the condition of the object Ob is being checked, portable terminal ID of the portable terminal unit TA as information indicating the portable terminal unit TA checking the condition of the object Ob, and sensor ID of the sensor unit SU sensing (shooting) the object Ob whose condition is being checked. The condition checking notification communication signal may house therein information indicating that the condition of the object Ob is being checked by LIVE video (LIVE video checking information).

In the LIVE video display mode, when receiving an input operation on the "end LIVE" button 527, the portable terminal unit TA ends the LIVE video display mode by the display processing section 4121 and the condition check processing section 4122 in the TA monitoring processing section 412, transits (returns) to the still image display mode, and transmits a condition check cancel notification communication signal for giving notification of the end of the condition check to the management server unit SV by the condition check processing section 4122 (C3). The condition check cancel notification communication signal houses therein condition check end information indicating the end of the condition check of the object Ob, portable terminal ID of the portable terminal unit TA as information indicating the portable terminal unit TA ending the condition check of the object Ob, and sensor ID of the sensor unit SU sensing (shooting) the object Ob whose condition check ends.

When receiving an input operation on the "talk" button 525 in the LIVE video display mode, the portable terminal unit TA ends the LIVE video display mode by the display processing section 4121 and the condition check processing section 4122 in the TA monitoring processing section 412, and transits to the call mode (C7). When receiving an input operation on the "action" button 524, the TA monitoring processing section 412 in the portable terminal unit TA keeps the still image display mode if a monitoring information screen 52a is present in addition to the monitoring information screen 52a displayed on the TA display section 46, and transits from the LIVE video display mode to the standby mode if a monitoring information screen 52a is not present in addition to the monitoring information screen 52a displayed on the TA display section 46 (C6-2).

The call mode is an operation mode of calling or making a call to an object Ob sensed by a sensor unit SU, and corresponds to other example of the condition check mode. When receiving an input operation on the "talk" button 525 in the processing in S18, the TA control processing section 41 in the portable terminal unit TA transits to the call mode, and as an example of the processing in S19, the portable terminal unit TA is connected to the sensor unit SU sensing the object Ob currently displayed on the TA display section 46 by the display processing section 4121 and the condition check processing section 4122 in the TA monitoring processing section 412 to be able to make a call via the network NW (C4), and the user (monitoring person) of the portable terminal unit TA can talk with the object Ob sensed by the sensor unit SU. A call screen 53 in the call mode includes the menu bar region 511, the object name region 521, the icon region 522, a call main region 531 for displaying therein a message indicating that a call is possible (such as "now calling") and an icon, the "action" button 524, and an "end" button 528. The "end" button 528 is directed for inputting a command to end the call mode. The condition check processing section 4122 in the portable terminal unit TA transmits a condition checking notification communication signal for notifying that the condition of the object Ob is being checked to the management server unit SV. The condition checking notification communication signal houses therein condition checking information indicating that the condition of the object Ob is being checked, portable terminal ID of the portable terminal unit TA as information indicating the portable terminal unit TA checking the condition of the object Ob, and sensor ID of the sensor unit SU sensing (shooting) the object Ob whose condition is being checked. The condition checking notification communication signal may house therein information indicating that the condition of the object Ob is being checked by calling (call checking information).

When receiving an input operation on the "end" button 528 in the call mode, the portable terminal unit TA ends the call mode by the display processing section 4121 and the condition check processing section 4122 in the TA monitoring processing section 412, transits (returns) to the still image display mode, and transmits a condition check cancel notification communication signal for giving notification of the end of the condition check to the management server unit SV by the condition check processing section 4122 (C5). The condition check cancel notification communication signal houses therein condition check end information indicating the end of the condition check of the object Ob, portable terminal ID of the portable terminal unit TA as information indicating the portable terminal unit TA ending the condition check of the object Ob, and sensor ID of the sensor unit SU sensing (shooting) the object Ob whose condition check ends.

When receiving an input operation on the "action" button 524 in the call mode, the TA monitoring processing section 412 in the portable terminal unit TA keeps the still image display mode if a monitoring information screen 52a is present in addition to the monitoring information screen 52a displayed on the TA display section 46, and transits from the call mode to the standby mode if a monitoring information screen 52a is not present in addition to the monitoring information screen 52a displayed on the TA display section 46 (C6-3).

As described above, when receiving an input operation on the "action" button 524 (C6-1, C6-2, C6-3), the action-related processing section 4123 in the TA monitoring processing section 412 in the portable terminal unit TA registers a flag "1" in action field 4237 in the record with the sensor ID corresponding to the monitoring information on the object Ob currently displayed on the TA display section 46 registered in sensor ID field 4231, transmits an action notification communication signal for notifying that the monitoring person (user) logging in the portable terminal unit TA receives an intention to actually perform an action on the object Ob currently displayed on the TA display section 46 to the management server unit SV, and deletes the monitoring information screen 52a for the object Ob displayed on the TA display section 46. The action notification communication signal houses therein action reception information indicating that the intention to actually perform an action on the object Ob is received, portable terminal ID of the portable terminal unit TA as information indicating the portable terminal unit TA receiving the intention to actually perform an action on the object Ob, and sensor ID corresponding to the monitoring information on the object Ob displayed on the TA display section 46 receiving an input operation on the "action" button 524 as information indicating the object Ob to be handled by the monitoring person.

Figure 10:
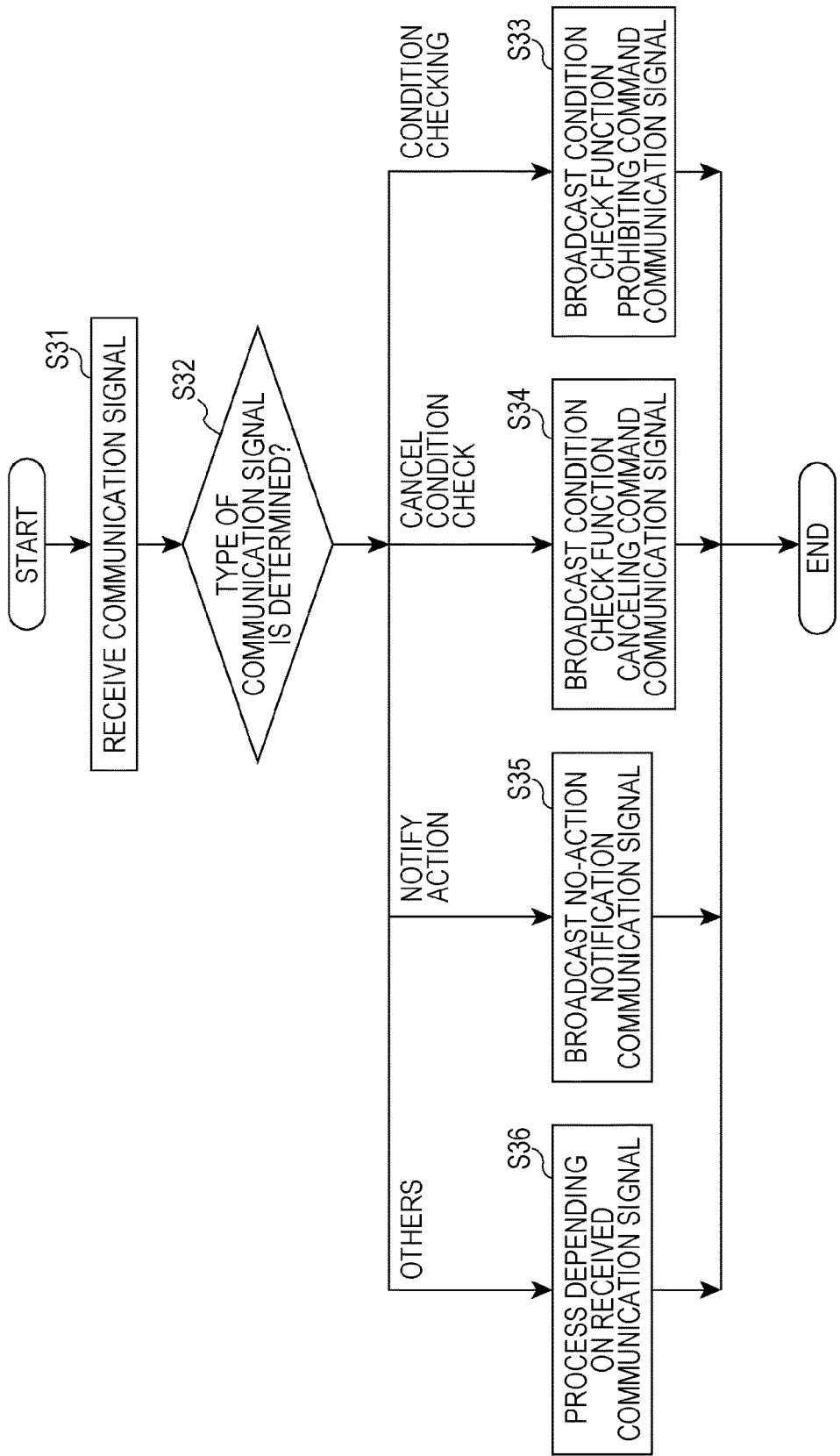
FIG. 10 is a flowchart illustrating the operations for association between portable terminal units in the monitoring server unit.

The operations of the management server unit SV when receiving a condition checking notification communication signal, a condition check cancel notification communication signal, and an action notification communication signal transmitted from a portable terminal unit TA to the management server unit SV as described above will be described below. FIG. 10 is a flowchart illustrating the operations for association between portable terminal units in the monitoring server unit.

In FIG. 10, when the SV communication IF section 13 in the management server unit SV receives a communication signal (S31), the SV monitoring processing section 112 determines the type of the received communication signal (S32). As a result of the determination, the management server unit SV performs the processing in S33 when the received communication signal is a condition checking notification communication signal (condition is being checked), performs the processing in S34 when the received communication signal is a condition check cancel notification communication signal (condition check is canceled), performs the processing in S35 when the received communication signal is an action notification communication signal (notification of action is given), and performs the processing in S36 when the received communication signal is not a condition checking notification communication signal, a condition check cancel notification communication signal, or an action notification communication signal.

In the processing in S33, at first, in order to store which monitoring person is checking a condition of which object Ob in the SV monitoring information storage section 121, the SV monitoring processing section 112 in the management server unit SV extracts the portable terminal ID and the sensor ID housed in the condition checking notification communication signal received in the processing in S31 as the information indicating the portable terminal unit TA (who) checking the condition of the object Ob and the information indicating the sensor unit SU (whom) used for checking a condition of the object Ob, respectively. The SV monitoring processing section 112 in the management server unit SV then searches a record in which the extracted sensor ID is registered in sensor ID field 4231 and a flag "0" is registered in condition checking field 4236 and action field 4237, and registers and updates the extracted portable terminal ID in condition checking field 4236 in the searched record. Thereby, a situation in which the user (monitoring person) of the portable terminal unit TA with the portable terminal ID is checking a condition of the object Ob sensed by the sensor unit SU with the sensor ID is registered in the monitoring information table MT, and the situation is stored in the SV monitoring information storage section 121. The SV communication IF 13 in the management server unit SV then broadcasts a condition check function prohibiting command communication signal for giving notification of a command to prohibit executing the condition check mode (the LIVE video display mode and the call mode according to the present embodiment) in order to notify the fixed terminal unit SP and the portable terminal units TA of the situation and to avoid other portable terminal unit TA from redundantly checking the condition of the object Ob. The condition check function prohibiting command communication signal houses therein information on a command to prohibit executing the condition check mode (condition check mode execution prohibiting command information), and houses therein the portable terminal ID and the sensor ID extracted from the condition checking notification communication signal as the information indicating the portable terminal unit TA (who) checking the condition of the object Ob and the information indicating the sensor unit SU (whose) to be prohibited from executing the condition check mode, respectively. The condition check function prohibiting command communication signal may house a type of the condition check mode used for checking a condition (the LIVE video checking information or the call checking information in the above example). The SV monitoring processing section 112 in the management server unit SV then stores each item of communication log information on reception of the condition checking notification communication signal and transmission of the condition check function prohibiting command communication signal in the communication log information storage section 123.

In the processing in S34, at first, in order to store which monitoring person ends the condition check of which object Ob in the SV monitoring information storage section 121, the SV monitoring processing section 112 in the management server unit SV extracts the portable terminal ID and the sensor ID housed in the condition check cancel notification communication signal received in the processing in S31 as the information indicating the portable terminal unit TA (who) ending the condition check of the object Ob and the information indicating the sensor unit SU (whom) whose condition check ends, respectively. The SV monitoring processing section 112 in the management server unit SV searches a record in which the extracted sensor ID and portable terminal ID are registered in sensor ID field 4231 and condition checking field 4236, respectively and a flag "0" is registered in action field 4237, and registers and updates a flag "0" in condition checking field 4236 in the searched record. Thereby, a situation in which the user (monitoring person) of the portable terminal unit TA with the portable terminal ID ends the condition check of the object Ob sensed by the sensor unit SU with the sensor ID is registered in the monitoring information table MT, and the situation is stored in the SV monitoring information storage section 121. Then in the management server unit SV, the SV communication IF 13 broadcasts a condition check function canceling command communication signal for giving notification of a command to cancel the prohibition of executing the condition check mode (the LIVE video display mode and the call mode according to the present embodiment) in order to notify the fixed terminal unit SP and the portable terminal units TA of the situation and to enable the other portable terminal units TA to check the condition of the object Ob. The condition check function canceling command communication signal houses the information on a command to cancel the prohibition of executing the condition check mode (the condition check mode execution canceling command information), and houses the portable terminal ID and the sensor ID extracted from the condition check cancel notification communication signal as the information indicating the portable terminal unit TA (who) ending the condition check of the object Ob and the information indicating the sensor unit SU (whose) for which the prohibition of executing the condition check mode is to be canceled, respectively. Then in the management server unit SV, the SV monitoring processing section 112 stores each item of communication log information on reception of the condition check cancel notification communication signal and transmission of the condition check function canceling command communication signal in the communication log information storage section 123.

In the processing in S35, at first, in order to store which monitoring person has an intention to perform the action such as nursing on which object Ob in the SV monitoring information storage section 121, the SV monitoring processing section 112 in the management server unit SV extracts the portable terminal ID and the sensor ID housed in the action notification communication signal received in the processing in S31 as the information indicating the monitoring person (who) of the portable terminal unit TA performing the action on the object Ob and the information indicating the object Ob (whom) sensed by the sensor unit SU on which the action is performed by the monitoring person. The SV monitoring processing section 112 in the management server unit SV then searches a record in which the extracted sensor ID and portable terminal ID are registered in sensor ID field 4231 and condition checking field 4236, respectively and a flag "0" is registered in action field 4237, and registers and updates a flag "0" and a flag "1" in condition checking field 4236 and action field 4237 in the searched record, respectively. Thereby, a situation in which the user (monitoring person) of the portable terminal unit TA with the portable terminal ID has an intention to perform the action on the object Ob sensed by the sensor unit SU with the sensor ID is registered in the monitoring information table MT, and the situation is stored in the SV monitoring information storage section 121. Then in the management server unit SV, the SV communication IF 13 broadcasts a no-action notification communication signal for notifying that the actual action is not required on the object Ob in order to notify the fixed terminal unit SP and the portable terminal units TA of the situation and to avoid other portable terminal unit TA from redundantly performing the action on the object Ob. The no-action notification communication signal houses the information (no-action information) indicating that the actual action is not required on the object Ob, and houses the portable terminal ID and the sensor ID extracted from the action notification communication signal as the information indicating the monitoring person (who) of the portable terminal unit TA having an intention to perform the action on the object Ob and the information indicating the object Ob (whose) sensed by the sensor unit SU for which the action is not required, respectively. The SV monitoring processing section 112 in the management server unit SV then stores each item of communication log information on reception of the action notification communication signal and transmission of the no-action notification communication signal in the communication log information storage section 123.

In the processing in S36, the SV monitoring processing section 112 in the management server unit SV performs an appropriate processing depending on the received communication signal and ends the operations along with reception of each communication signal.

The management server unit SV may notify the fixed terminal unit SP or the portable terminal units TA of the fact that an intention to perform the action is not present when there is a record in which a predetermined time (such as 5 minutes, 10 minutes, or 20 minutes) elapses after a determination time and an intention to perform the action is not present with reference to the monitoring information table MT stored in the SV monitoring information storage section 121. More specifically, the SV monitoring processing section 112 in the management server unit SV searches a record in which a determination time after which the predetermined time or more elapses is registered in determination time field 4233 and a flag "0" is registered in action field 4237 from the monitoring information table MT, and extracts the sensor ID from sensor ID field 4231 of the searched record. Then in the management server unit SV, the SV communication IF section broadcasts a communication signal (no-action alarm communication signal) housing the sensor ID extracted by the SV monitoring processing section 112 as the information (no-action information) indicating that an action is not performed and the information indicating that the object is not handled Thereby, a duration of the no-action state is shortened, and the stress on the object Ob is reduced. At this time, the SV monitoring processing section 112 in the management server unit SV may be configured to examine whether the flag registered in action field 4237 is true with reference to the communication log information. Thereby, a duration of the no-action state can be shortened more accurately.

Figure 11:
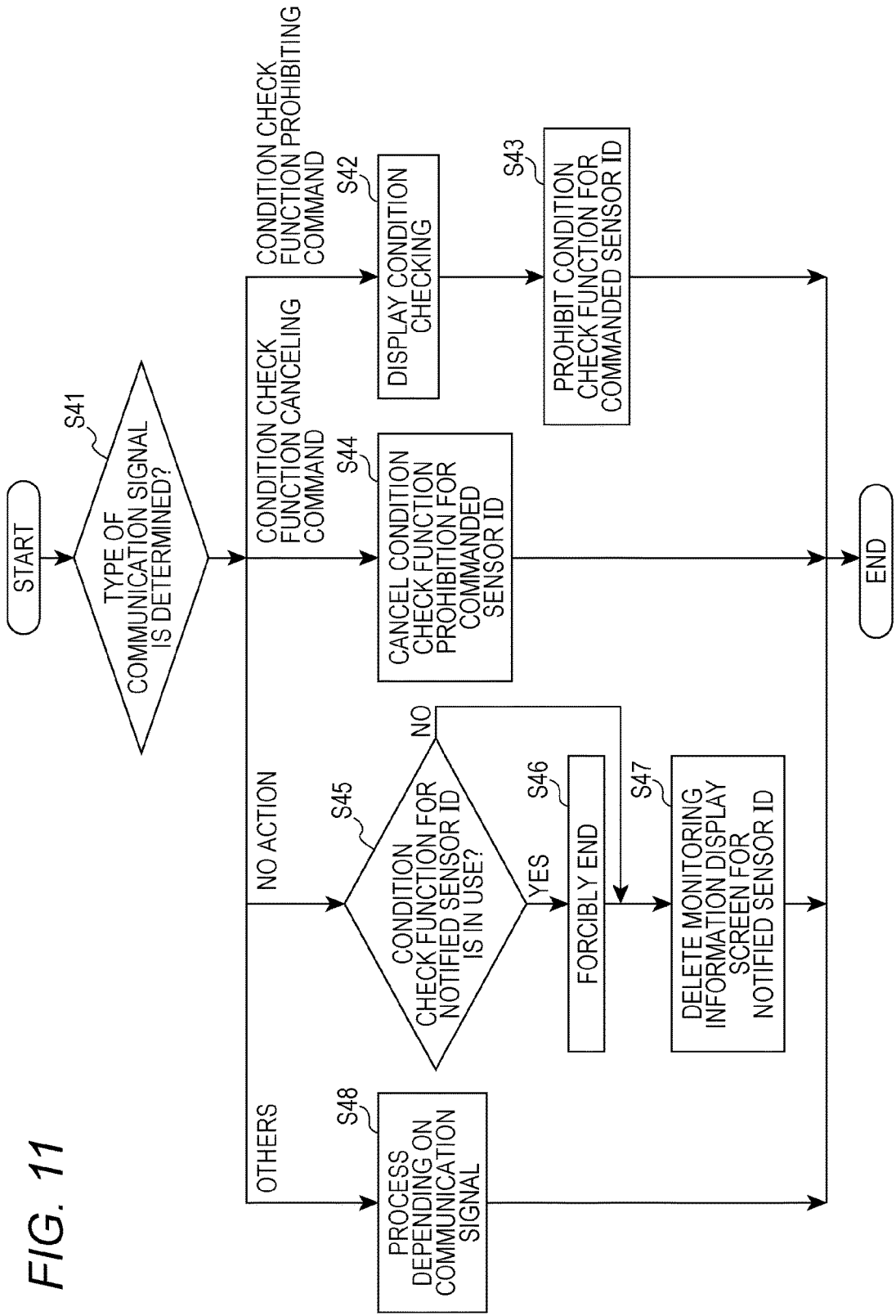
FIG. 11 is a flowchart illustrating the operations for association between portable terminal units in the portable terminal unit.

An operation of the portable terminal unit TA when receiving a condition check function prohibiting command communication signal, a condition check function canceling command communication signal, and a no-action notification communication signal broadcasted from the management server unit SV as described above will be described below. The operation is performed as one processing in the processing in S21 described with reference to FIG. 5. FIG. 11 is a flowchart illustrating the operations for association between portable terminal units in the portable terminal unit.

In FIG. 11, the TA monitoring processing section 412 in the portable terminal unit TA determines the type of the received communication signal (S41). As a result of the determination, the portable terminal unit TA performs the processing in S42 when the received communication signal is a condition check function prohibiting command communication signal (condition check function prohibiting command), performs the processing in S44 when the received communication signal is a condition check function canceling command communication signal (condition check function canceling command), performs the processing in S45 when the received communication signal is a no-action notification communication signal (no action), and performs the processing in S48 when the received communication signal is not a condition check function prohibiting command communication signal, a condition check function canceling command communication signal or a no-action notification communication signal. Here, when the portable terminal ID of the portable terminal unit TA is housed in the condition check function prohibiting command communication signal, the condition check function canceling command communication signal, and the no-action notification communication signal, the communication signals are not required in the portable terminal unit TA, and the operation along with each of the communication signals ends, and the next processing in S42 to the processing in S48 are not performed.

In the processing in S42, at first, in order to store which monitoring person is checking a condition of which object Ob in the TA monitoring information storage section 422, the TA monitoring processing section 412 in the portable terminal unit TA extracts the portable terminal ID and the sensor ID housed in the condition check function prohibiting command communication signal received in the processing in S12 as the information indicating the portable terminal unit TA (who) checking the condition of the object Ob and the information indicating the sensor unit SU (whom) used for checking the condition of the object Ob, respectively. The TA monitoring processing section 412 in the portable terminal unit TA then searches a record in which the extracted sensor ID is registered in sensor ID field 4231 and a flag "0" is registered in condition checking field 4236 and action field 4237, and registers and updates the extracted portable terminal ID in condition checking field 4236 in the searched record. Thereby, a situation in which the user (monitoring person) of the portable terminal unit TA with the portable terminal ID is checking a condition of the object Ob sensed by the sensor unit SU with the sensor ID is registered in the monitoring information table MT, and the situation is stored in the TA monitoring information storage section 422. Then in the portable terminal unit TA, the display processing section 4121 in the TA monitoring processing section 412 displays the condition checking screen 54 of other unit (see FIG. 12 described below) indicating that the condition of the object Ob is being checked by other portable terminal unit TA on the TA display section 46. The condition checking screen 54 of other unit includes the menu bar region 511, the object name region 521, the icon region 522, the image region 523a, and the condition checking main region 541 displaying a message that a condition of the object Ob is being checked by other portable terminal unit TA (such as "person ○○, LIVE checking").

In order to avoid the portable terminal unit TA from redundantly checking the condition of the object Ob, the condition check processing section 4122 in the TA monitoring processing section 412 in the portable terminal unit TA prohibits the condition of the object Ob designated in the received condition check function prohibiting command communication signal from being checked (S43), and ends the operation along with reception of each communication signal. More specifically, when a command to execute the condition check mode is input or when an input operation on the "talk" button 525 or the "view LIVE" button 526 is received according to the present embodiment, the condition check processing section 4122 refers to condition checking field 4236 in the record in which the sensor ID for the monitoring information screen 52 receiving the input operation is registered in sensor ID field 4231 and a flag "0" is registered in action field 4237, disables the input operation and does not execute a condition check mode (the call mode or the LIVE video display mode in the example) when the portable terminal ID of other portable terminal unit TA is registered in condition checking field 4236 referred to. Here, the display processing section 4121 refers to condition checking field 4236 when displaying the monitoring information screen 52, and displays the "talk" button 525 and the "view LIVE" button 526 in the monitoring information screen 52 in a different form from the input-enabled state when the portable terminal ID of other portable terminal unit TA is registered in condition checking field 4236 referred to, thereby displaying that an input operation on the "talk" button 525 and the "view LIVE" button 526 is not possible (input-disabled state). The input-disabled state is displayed in grayout or by blinking, for example. On the other hand, when a flag "0" is registered in condition checking field 4236 referred to, the condition check processing section 4122 enables the input operation and executes a condition check mode (the call mode or the LIVE video display mode in the example).

In the processing in S44, at first, in order to store which monitoring person ends the condition check of which object Ob in the TA monitoring information storage section 422, the TA monitoring processing section 412 in the portable terminal unit TA extracts the portable terminal ID and the sensor ID housed in the condition check function canceling command communication signal received in the processing in S12 as the information indicating the portable terminal unit TA (who) ending the condition check of the object Ob and the information indicating the sensor unit SU (whom) whose condition check ends, respectively. The TA monitoring processing section 412 in the portable terminal unit TA then searches a record in which the extracted sensor ID and portable terminal ID are registered in sensor ID field 4231 and condition checking field 4236, respectively and a flag "0" is registered in action field 4237, and registers and updates a flag "0" in condition checking field 4236 in the searched record. Thereby, a situation in which the user (monitoring person) of the portable terminal unit TA with the portable terminal ID ends the condition check of the object Ob sensed by the sensor unit SU with the sensor ID is registered in the monitoring information table MT, and the situation is stored in the TA monitoring information storage section 422. Then, a flag "0" is registered in condition checking field 4236, and thus the condition check mode can be executed and its prohibition is canceled. Therefore, the user (monitoring person) of the portable terminal unit TA can check a condition of the object Ob for which the condition check is prohibited and then its prohibition is canceled as needed. The portable terminal unit TA then ends the operation along with reception of each communication signal.

In the processing in S45, at first, in order to store which monitoring person has an intention to perform the action such as nursing on which object Ob in the TA monitoring information storage section 422, the TA monitoring processing section 412 in the portable terminal unit TA extracts the portable terminal ID and the sensor ID housed in the no-action notification communication signal received in the processing in S12 as the information indicating the monitoring person (who) of the portable terminal unit TA performing the action on the object Ob and the information indicating the object Ob (whom) sensed by the sensor unit SU on which the monitoring person performs the action, respectively. The action-related processing section 4123 in the portable terminal unit TA then determines whether the operation of checking a condition of the object Ob sensed by the sensor unit SU with the extracted sensor ID is being performed by use of the sensor unit SU with the sensor ID extracted by the condition check processing section 4122. As a result of the determination, when the condition check operation is not being performed (No), the action-related processing section 4123 performs the processing in S47, on the other hand, as a result of the determination, when the condition check operation is being performed (Yes), the action-related processing section 4123 forcibly ends the operation of the condition check processing section 4122 in execution (S46), and performs the processing in S47.

In the processing in S47, the action-related processing section 4123 in the portable terminal unit TA deletes (erases) the monitoring information screen for the extracted sensor ID from the display screen storage section 421. The TA monitoring processing section 412 in the portable terminal unit TA then searches a record in which the extracted sensor ID and portable terminal ID are registered in sensor ID field 4231 and condition checking field 4236, respectively and a flag "0" is registered in action field 4237, and registers and updates a flag "0" and a flag "1" in condition checking field 4236 and action field 4237 in the searched record, respectively. Thereby, a situation in which the user (monitoring person) of the portable terminal unit TA with the portable terminal ID has an intention to perform the action on the object Ob sensed by the sensor unit SU with the sensor ID is registered in the monitoring information table MT, and the situation is stored in the TA monitoring information storage section 422. The portable terminal unit TA ends the operation along with reception of each communication signal.

In the processing in S48, the TA monitoring processing section 412 in the portable terminal unit TA performs an appropriate processing depending on the received communication signal, and ends the operation along with reception of each communication signal.

Figure 12:
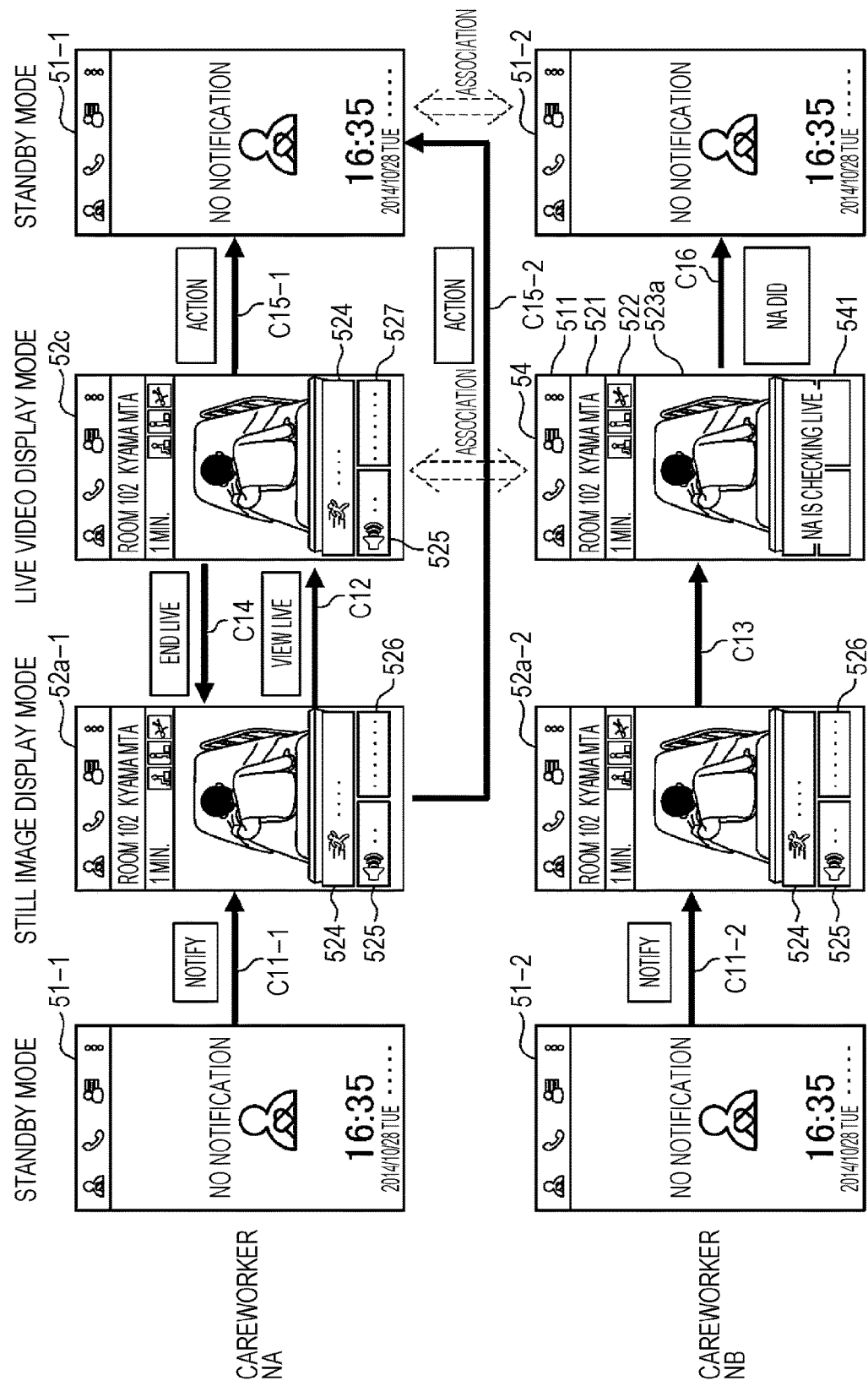
FIG. 12 is a sequence diagram for explaining an association operation between two portable terminal units by way of example.

An operation of associating portable terminal units will be described below by way of example. FIG. 12 is a sequence diagram for explaining an operation of associating two portable terminal units as an example.

In the specific example, the association operation will be described in terms of the first portable terminal unit TA-1 handled by a careworker NA and the second portable terminal unit TA-2 handled by a careworker NB among a plurality of portable terminal units TA as illustrated in FIG. 1 and FIG. 12. The specific example assumes that only the monitoring information by the sensor unit SU-2 is present and other monitoring information is not present. The portable terminal IDs of the first and second portable terminal units TA-1 and TA-2 are TA-1 and TA-2, respectively, and the sensor ID of the second sensor unit SU-2 sensing the object Ob-2 (person B) is SU-2.

In FIG. 12, when the careworker NA logs in the first portable terminal unit TA-1, the first portable terminal unit TA-1 displays the standby screen 51-1 on the TA display section 46-1 in the processing in S11, and when the careworker NB logs in the second portable terminal unit TA-2, the second portable terminal unit TA-2 displays the standby screen 51-2 on the TA display section 46-2 in the processing in S11. In the description, when the components in the first portable terminal unit TA-1 need to be discriminated from the components in the second portable terminal unit TA-2, the reference numerals of the components in the first portable terminal unit TA-1 are added with a subscript of "-1" and the reference numerals of the components in the second portable terminal unit TA-2 are added with a subscript of "-2."

When the sensor unit SU-2 sensing the object Ob-2 (person B) determines a state (condition) of the object Ob-2 by the above operation, and transmits a monitoring information communication signal, the monitoring information communication signal is received by the portable terminal units TA-1 and TA-2 via the management server unit SV.

When receiving the monitoring information communication signal, the first portable terminal unit TA-1 displays the monitoring information screen 52a-1 for the object Ob-2 (the sensor unit SU-2 with the sensor ID of SU-2) on the TA display section 46-1 (C11-1) in the processing in S12 to the processing in S16. Similarly, the second portable terminal unit TA-2 displays the monitoring information screen 52a-2 for the object Ob-2 on the TA display section 46-2 in the processing in S12 to the processing in S16 (C11-2).

When the careworker NA performs an input operation on the "view LIVE" button 526 in the first portable terminal unit TA-1, the first portable terminal unit TA-1 displays the monitoring information screen 52c having the image region 523a displaying an animation therein on the TA display section 46-1 and transmits a condition checking notification communication signal housing the sensor ID of SU-2 and the portable terminal ID of TA-1 therein to the management server unit SV in the processing in S18 and the processing in S19 (C12).

When receiving the condition checking notification communication signal, the management server unit SV broadcasts a condition check function prohibiting command communication signal housing therein the sensor ID of SU-2 and the portable terminal ID of TA-1 in the processing in S31 to the processing in S33.

When receiving the condition check function prohibiting command communication signal, the first portable terminal unit TA-1 ignores it and the second portable terminal unit TA-2 displays the condition checking screen 54 of the other unit having the checking information on the TA display section 46-2 and prohibits the condition check function of the sensor unit SU-2 with the sensor ID of SU-2 in the processing in S41 to the processing in S43. Thereby, the first and second portable terminal units TA-1 and TA-2 are associated with each other.

When the careworker NA performs an input operation on the "end LIVE" button 527 in the first portable terminal unit TA-1, the first portable terminal unit TA-1 returns one step back and displays the monitoring information screen 52a-1 having the image region 523a displaying a still image therein on the TA display section 46-1, and transmits a condition check cancel notification communication signal housing the sensor ID of SU-2 and the portable terminal ID of TA-1 therein to the management server unit SV in the processing in S18 and the processing in S19 (C14).

When receiving the condition check cancel notification communication signal, the management server unit SV broadcasts a condition check function canceling command communication signal housing the sensor ID of SU-2 and the portable terminal ID of TA-1 therein in the processing in S31, the processing in S32, and the processing in S34.

When receiving the condition check function canceling command communication signal, the first portable terminal unit TA-1 ignores it and the second portable terminal unit TA-2 returns one step back, displays the monitoring information screen 52a-2 for the sensor unit SU-2 with the sensor ID of SU-2 on the TA display section 46-2 and cancels the prohibition of the condition check function of the sensor unit SU-2 with the sensor ID of SU-2 (not illustrated) in the processing in S41 and the processing in S44. Thereby, the first and second portable terminal units TA-1 and TA-2 are associated with each other.

On the other hand, when the careworker NA performs an input operation on the "action" button 524 in the first portable terminal unit TA-1 on the monitoring information screen 52a-1 or 52c displaying a still image or animation, the first portable terminal unit TA-1 transmits an action notification communication signal housing the sensor ID of SU-2 and the portable terminal ID of TA-1 therein to the management server unit SV, and displays the standby screen 51-1 on the TA display section 46-1 in the processing in S18 and the processing in S19 (C15-1, C15-2).

When receiving the action notification communication signal, the management server unit SV broadcasts a no-action notification communication signal housing the sensor ID of SU-2 and the portable terminal ID of TA-1 therein in the processing in S31, the processing in S32, and the processing in S35.

When receiving the no-action notification communication signal, the first portable terminal unit TA-1 ignores it and the second portable terminal unit TA-2 deletes the monitoring information screen 52a-2 for the sensor unit SU-2 with the sensor ID of SU-2 and displays the standby screen 51-2 on the TA display section 46-2 in the processing in S41, the processing in S45, the processing in S46, and the processing in S47 (C16). Thereby, the first and second portable terminal units TA-1 and TA-2 are associated with each other.

As described above, with the object monitoring system MS according to the present embodiment, the management server unit SV and the method therefor, and the portable terminal units TA and the method therefor, when other portable terminal unit TA is checking a condition of an object Ob in a condition check mode such as the LIVE video display mode or the call mode, the condition check mode for the object Ob is prohibited from being executed, and also when monitoring information is notified to the portable terminal units TA, the condition of the object Ob based on the monitoring information is not redundantly checked in the condition check mode. Thus, the user (monitoring person) handling one portable terminal unit TA can be promoted to actually perform an action on the object Ob. Therefore, with the object monitoring system MS, the management server unit SV and the method therefor, and the portable terminal units TA and the method therefor, a condition check state of an object Ob can be mutually shared, and an action depending on a condition of the object Ob can be performed at a more appropriate timing.

With the object monitoring system MS according to the present embodiment, the management server unit SV and the method therefor, and the portable terminal units TA and the method therefor, before one portable terminal unit TA or other portable terminal unit TA receives an intention to actually perform an action on the object Ob based on the monitoring information, when the other portable terminal unit TA ends the condition check of the object Ob based on the monitoring information, the prohibition of executing the condition check mode on the object Ob based on the monitoring information is canceled, and thus when the user (monitoring person Y) handling the other portable terminal unit TA does not have an intention to perform the action, the user (monitoring person X) of the portable terminal unit TA can recognize the situation, and can check the condition of the object Ob for which the condition check is prohibited and then the prohibition is canceled as needed.

With the object monitoring system MS according to the present embodiment, the management server unit SV and the method therefor, and the portable terminal units TA and the method therefor, the checking information is displayed, and thus the user (monitoring person X) of the portable terminal unit TA can recognize that the user (monitoring person Y) of the other portable terminal unit is checking.

With the object monitoring system MS according to the present embodiment, the management server unit SV and the method therefor, and the portable terminal units TA and the method therefor, when the user (monitoring person Y) handling the other portable terminal unit TA has an intention to perform the action, the condition check mode in execution in the portable terminal unit TA is forcibly terminated, and the unnecessary condition check of the object Ob can be terminated.

The portable terminal units TA have been described above, but the fixed terminal unit SP may have the similar functions and the fixed terminal unit SP may be other exemplary terminal apparatus, and the portable terminal units TA can be associated with the fixed terminal unit SP.

The specification discloses various forms of techniques as described above, and main techniques among them will be summarized below.

A terminal apparatus for an object monitoring system according to one aspect is directed for receiving and displaying monitoring information on an object in the object monitoring system for sensing and give notification of a predetermined motion of the object to be monitored and monitoring the object, has a plurality of operation modes including a condition check mode of checking a condition of the object until receiving an intention to actually perform an action on the object based on the monitoring information after receiving the monitoring information, and prohibits executing the condition check mode on the object based on the received monitoring information while other terminal apparatus is checking the condition of the object based on the received monitoring information in the condition check mode. According to other aspect, a terminal apparatus for an object monitoring system is preferably a terminal apparatus in an object monitoring system for monitoring an object, the object monitoring system including a sensor apparatus for sensing the object to be monitored, a central processing apparatus communicably connected to the sensor apparatus and directed for managing monitoring information on the object based on a sensing result received from the sensor apparatus, and a plurality of terminal apparatuses communicably connected to the central processing apparatus and directed for receiving and displaying the monitoring information, the terminal apparatus including a communication section for making communication, a display section for displaying, an input section for receiving an input operation, a condition check processing section for checking a condition of the object, and a display processing section for, when the communication section receives a monitoring information communication signal housing the monitoring information therein, displaying the monitoring information housed in the monitoring information communication signal on the display section, in which the condition check processing section prohibits an operation of checking a condition of the object based on the monitoring information when the communication section receives a condition check function prohibiting command communication signal for giving notification of a command to prohibit checking a condition of the object based on the monitoring information. According to other aspect, preferably the terminal apparatus for an object monitoring system has a plurality of operation modes including a condition check mode of checking a condition of the object until receiving an intention to actually perform an action on the object based on the monitoring information after receiving the monitoring information, and prohibits executing the condition check mode on the object based on the received monitoring information when the communication section receives a condition check function prohibiting command communication signal for giving notification of a command to prohibit checking a condition of the object based on the monitoring information while other terminal apparatus is executing the condition check mode in order to check a condition of the object based on the received monitoring information.

The terminal apparatus prohibits executing the condition check mode on the object based on the monitoring information while other terminal apparatus is checking the condition of the object based on the monitoring information in the condition check mode, and thus does not redundantly check the condition of the object based on the monitoring information even when a plurality of terminal apparatuses are notified of the monitoring information. Thus, one user (monitoring person) handling one terminal apparatus can be promoted to actually perform an action on the object. Therefore, the terminal apparatus enables a checked condition of an object to be mutually shared and an action depending on a condition of an object to be performed at a more appropriate timing.

According to other aspect, before one terminal apparatus or other terminal apparatus receives an intention to actually perform an action on the object based on the monitoring information, when the other terminal apparatus ends the condition check of the object based on the received monitoring information, the terminal apparatus for an object monitoring system cancels the prohibition of executing the condition check mode on the object based on the received monitoring information. According to other aspect, preferably in the terminal apparatus for an object monitoring system, when the communication section receives a condition check function canceling command communication signal for giving notification a command to cancel the prohibition based on the monitoring information before the communication section receives an intention to actually perform an action on the object based on the monitoring information from the input section or receives a no-action notification communication signal for notifying that an intention to actually perform an action on the object based on the monitoring information is received by other terminal apparatus, the condition check processing section cancels the prohibition based on the monitoring information.

Before one terminal apparatus or other terminal apparatus receives an intention to actually perform an action on the object based on the monitoring information, when the other terminal apparatus ends the condition check of the object based on the monitoring information, the terminal apparatus cancels the prohibition of executing the condition check mode on the object based on the monitoring information, and thus when the user (monitoring person) handling the other terminal apparatus does not have an intention to perform the action, the user (monitoring person) of the terminal apparatus can recognize the situation and can check a condition of the object for which the condition check is prohibited and then the prohibition is canceled as needed.

According to other aspect, the terminal apparatus for an object monitoring system displays checking information indicating that other terminal apparatus is checking a condition of the object based on the received monitoring information while the other terminal apparatus is checking the condition of the object based on the received monitoring information in the condition check mode. According to other aspect, preferably in the terminal apparatus for an object monitoring system, when the communication section receives the condition check function prohibiting command communication signal, the display processing section displays checking information indicating that other terminal apparatus is checking the condition of the object based on the monitoring information on the display section.

The checking information is displayed, and thus the user (monitoring person) of the terminal apparatus can recognize that the user (monitoring person) of other terminal apparatus is checking.

According to other aspect, in the terminal apparatus for an object monitoring system, when the other terminal apparatus receives an intention to actually perform an action on the object based on the monitoring information, the screen displaying the monitoring information thereon is erased.

The terminal apparatus can achieve mutual association between terminal apparatuses.

Further, according to other aspect, the terminal apparatus for an object monitoring system forcibly ends the condition check mode in execution when the other terminal apparatus receives an intention to actually perform an action on the object based on the received monitoring information while a condition of the object based on the received monitoring information is being checked in the condition check mode. According to other aspect, preferably, the terminal apparatus for an object monitoring system further includes an action-related processing section for forcibly ending an operation of the condition check processing section in execution when the operation of checking a condition of the object based on the monitoring information of the condition check processing section is in execution and the communication section receives the no-action notification communication signal.

When the user (monitoring person) handling the other terminal apparatus has an intention to perform the action, the terminal apparatus forcibly ends the condition check mode in execution, and thus can end the unnecessary condition check of the object.

According to other aspect, the terminal apparatus for an object monitoring system has a plurality of operation modes including a condition check mode of checking a condition of the object, and the condition check mode is at least any of displaying an animation shooting the object on the display section, calling the object by an audio I/O section of the terminal apparatus, and talking with the object.

A terminal processing method for an object monitoring system according to other aspect is directed for receiving and displaying monitoring information on an object in the object monitoring system for sensing and giving notification of a predetermined motion of the object to be monitored and monitoring the object, has a plurality of operation modes including a condition check mode of checking a condition of the object until receiving an intention to actually perform an action on the object based on the monitoring information after receiving the monitoring information, and prohibits executing the condition check mode on the object based on the received monitoring information while other terminal apparatus is checking the condition of the object based on the received monitoring information in the condition check mode. According to other aspect, a terminal processing method for an object monitoring system is a terminal processing method for the terminal apparatus in an object monitoring system for monitoring an object, the object monitoring system including a sensor apparatus for sensing the object to be monitored, a central processing apparatus communicably connected to the sensor apparatus and directed for managing monitoring information on the object based on a sensing result received from the sensor apparatus, and a plurality of terminal apparatuses communicably connected to the central processing apparatus and directed for receiving and displaying the monitoring information, the terminal processing method including a condition check processing step of checking a condition of the object, and a display processing step of displaying the monitoring information housed in a monitoring information communication signal on a display section when a communication section receives the monitoring information communication signal housing the monitoring information therein, in which the condition check processing step of checking a condition of the object based on the monitoring information is prohibited from being performed when the communication section receives a condition check function prohibiting command communication signal for giving notification of a command to prohibit checking a condition of the object based on the monitoring information.

With the terminal processing method, while other terminal apparatus is checking a condition of the object based on the monitoring information in the condition check mode, the condition check mode on the object based on the monitoring information is prohibited from being executed, and thus even when a plurality of terminal apparatuses are notified of the monitoring information, the condition of the object based on the monitoring information is not redundantly checked in the condition check mode. Thus, one user (monitoring person) handling one terminal apparatus can be promoted to actually perform an action on the object. Therefore, the terminal processing method enables a checked condition of an object to be mutually shared and an action depending on a condition of an object to be performed at a more appropriate timing.

A central processing apparatus for an object monitoring system according to other aspect is directed for managing monitoring information on an object in the object monitoring system for sensing and giving notification of a predetermined motion of the object to be monitored and monitoring the object, and when receiving a condition checking notification communication signal for notifying that a condition of the object based on the monitoring information is being checked in the condition check mode of checking a condition of the object from a terminal apparatus among a plurality of terminal apparatuses, transmits a condition check function prohibiting command communication signal for giving notification of a command to prohibit executing the condition check mode based on the monitoring information to the other terminal apparatuses except the terminal apparatus among the terminal apparatuses. According to other aspect, a central processing apparatus for an object monitoring system is preferably a central processing apparatus in an object monitoring system for monitoring an object, the object monitoring system including a sensor apparatus for sensing the object to be monitored, a central processing apparatus communicably connected to the sensor apparatus and directed for managing monitoring information on the object based on a sensing result received from the sensor apparatus, and a plurality of terminal apparatuses communicably connected to the central processing apparatus and directed for receiving and displaying the monitoring information, the central processing apparatus including a communication section for making communication, and a monitoring processing section for managing the monitoring information, in which when the communication section receives a condition checking notification communication signal for notifying that a condition of the object based on the monitoring information is being checked by a condition check processing section for checking a condition of the object from a terminal apparatus among the terminal apparatuses, the monitoring processing section transmits a condition check function prohibiting command communication signal for giving notification of a command to prohibit checking a condition of the object based on the monitoring information to the other terminal apparatuses except the terminal apparatus among the terminal apparatuses by the communication section.

According to other aspect, in the central processing apparatus for an object monitoring system, the screen displaying the monitoring information thereon is erased when the other terminal apparatuses receive an intention to actually perform an action on the object based on the monitoring information.

The central processing apparatus can achieve mutual association between terminal apparatuses.

A central processing method for an object monitoring system according to other aspect is directed for managing monitoring information on an object in the object monitoring system for sensing and giving notification of a predetermined motion of the object to be monitored and monitoring the object, and when receiving a condition checking notification communication signal for notifying that a condition of the object based on the monitoring information is being checked in a condition check mode of checking a condition of the object from a terminal apparatus among a plurality of terminal apparatuses, transmits a condition check function prohibiting command communication signal for giving notification of a command to prohibit executing the condition check model based on the monitoring information to the other terminal apparatuses except the terminal apparatus among the terminal apparatuses. According to other aspect, a central processing method for an object monitoring system is preferably a central processing method in an object monitoring system for monitoring an object, the object monitoring system including a sensor apparatus for sensing the object to be monitored, a central processing apparatus communicably connected to the sensor apparatus and directed for managing monitoring information on the object based on a sensing result received from the sensor apparatus, and a plurality of terminal apparatuses communicably connected to the central processing apparatus and directed for receiving and displaying the monitoring information, the central processing method including a monitoring processing step of managing the monitoring information, in which the monitoring processing step includes a prohibiting command step of, when a communication section receives a condition checking notification communication signal for notifying that a condition of the object based on the monitoring information is being checked by a condition check processing section for checking a condition of the object from a terminal apparatus among the terminal apparatuses, transmitting a condition check function prohibiting command communication signal for giving notification of a command to prohibit checking a condition of the object based on the monitoring information to the other terminal apparatuses except the terminal apparatus among the terminal apparatuses by the communication section.

With the central processing apparatus and central processing method for an object monitoring system, when the condition checking notification communication signal is received, the condition check function prohibiting command communication signal is transmitted, and thus even when to a plurality of terminal apparatuses are notified of the monitoring information, the condition of the object based on the monitoring information is not redundantly checked in the condition check mode. Thus, one user (monitoring person) handling one terminal apparatus can be promoted to actually perform an action on the object. Therefore, the central processing apparatus and central processing method enable a checked condition of an object to be mutually shared and an action depending on a condition of an object to be performed at a more appropriate timing.

According to other aspect, with the central processing method for an object monitoring system, the screen displaying the monitoring information thereon is erased when the other terminal apparatuses receive an intention to actually perform an action on the object based on the monitoring information.

The central processing method can achieve mutual association between terminal apparatuses.

An object monitoring system according to other aspect is directed for sensing and giving notification of a predetermined motion of an object to be monitored and monitoring the object, and includes any of the above terminals for receiving and displaying monitoring information on the object and the above central processing apparatus for managing the monitoring information.

The object monitoring system enables a checked condition of an object to be mutually shared and an action depending on a condition of an object to be performed at a more appropriate timing.

According to other aspect, in the object monitoring system, the screen displaying the monitoring information thereon is erased when the other terminal apparatuses receive an intention to actually perform an action on the object based on the monitoring information.

The object monitoring system can achieve mutual association between terminal apparatuses.

The application is based on Japanese Patent Application No. 2015-65285 filed on Mar. 26, 2015, the contents of which are included in the present application.

The present invention has been described appropriately and sufficiently by way of the embodiment with reference to the drawings in order to express the present invention, and those skilled in the art should recognize that the embodiment can be easily changed and/or modified. Thus, a changed form or modified form by those skilled in the art is assumed as encompassed in the scope of claims without departing from the scope of claims

INDUSTRIAL APPLICABILITY

According to the present invention, it is possible to provide a terminal apparatus and terminal processing method for an object monitoring system, a central processing apparatus and central processing method for the object monitoring system, and the object monitoring system.

The invention claimed is:

1. An object monitoring method for an object monitoring system that includes a plurality of sensor units, a management server unit, and a plurality of terminal units that are communicably connected to each other via a network, the plurality of sensor units being provided corresponding to a plurality of objects to be monitored, and the object monitoring system monitoring the plurality of objects for nursing, care, or help by corresponding each of the plurality of sensor units to an object of the plurality of objects,
a sensor unit of the plurality of sensor units sensing a predetermined motion of an object corresponding to the sensor unit and generating an image, the management server unit receiving a sensing result on the object from the sensor unit and managing monitoring information on monitoring of the object, and a terminal unit of the plurality of terminal units receiving the monitoring information from the management server unit, displaying the monitoring information, and making an audio call, the method comprising:
receiving the monitoring information, by the terminal unit, from the management server unit via the network;
displaying the monitoring information received in the receiving on the terminal unit; and
processing one of first input operation, second input operation, and third input operation, wherein
in the processing of the first input operation, the terminal unit receives the first input operation for inputting a command to make communicable connection with the sensor unit corresponding to the object based on the monitoring information via the network, communicably connects the sensor unit corresponding to the object based on the monitoring information with the terminal unit via the network, and displays that a condition of the object based on the monitoring information is being checked on other terminal units except the terminal unit that has received the first input operation,
in the processing of the second input operation, the terminal unit receives the second input operation for inputting a command to display an animation shot by the sensor unit corresponding to the object based on the monitoring information, makes connection with the sensor unit corresponding to the object based on the monitoring information via the network to allow downloading of an animation, reproduces the animation on the terminal unit, and displays that the condition of the object based on the monitoring information is being checked on the other terminal units except the terminal unit that has received the second input operation, and
in the processing of the third input operation, the terminal unit receives the third input operation for inputting an intention to actually perform an action on the object based on the monitoring information, and causes the plurality of terminal units to transit to a standby mode.

2. The object monitoring method according to claim 1, wherein the processing of the first input operation further includes disabling the first input operation in the other terminal units except the terminal unit that has received the first input operation.

3. The object monitoring method according to claim 2, wherein the processing of the first input operation further includes receiving, by the terminal unit that has received the first input operation, a fourth input operation for inputting a command for ending the audio call and cancels the disablement of the first input operation in the other terminal units except the terminal unit that has received the fourth input operation.

4. The object monitoring method according to claim 3, further comprising forcibly ending the audio call of the terminal unit that has received the first input operation when a terminal unit among the other terminal units except the terminal unit that has received the first input operation receives the third input operation.

5. The object monitoring method according to claim 4, wherein forcibly ending the audio call further includes disabling the second input operation in the other terminal units except the terminal unit that has received the second input operation.

6. The object monitoring method according to claim 3, further comprising forcibly ending reproduction of the animation on the terminal unit that has received the second input operation when a terminal unit among the other terminal units except the terminal unit that has received the second input operation receives the third input operation.

7. The object monitoring method according to claim 6, wherein forcibly ending the audio call further includes disabling the second input operation in the other terminal units except the terminal unit that has received the second input operation.

8. The object monitoring method according to claim 2, further comprising forcibly ending the audio call of the terminal unit that has received the first input operation when a terminal unit among the other terminal units except the terminal unit that has received the first input operation receives the third input operation.

9. The object monitoring method according to claim 8, wherein forcibly ending the audio call further includes disabling the second input operation in the other terminal units except the terminal unit that has received the second input operation.

10. The object monitoring method according to claim 2, further comprising forcibly ending reproduction of the animation on the terminal unit that has received the second input operation when a terminal unit among the other terminal units except the terminal unit that has received the second input operation receives the third input operation.

11. The object monitoring method according to claim 1, further comprising forcibly ending the audio call of the terminal unit that has received the first input operation when a terminal unit among the other terminal units except the terminal unit that has received the first input operation receives the third input operation.

12. The object monitoring method according to claim 11, wherein forcibly ending the audio call further includes disabling the second input operation in the other terminal units except the terminal unit that has received the second input operation.

13. The object monitoring method according to claim 12, wherein in the forcibly ending the audio call, the terminal unit that has received the second input operation further receives a fifth input operation for inputting a command for ending reproduction of the animation and cancels the disablement of the second input operation in the other terminal units except the terminal unit that has received the fifth input operation.

14. The object monitoring method according to claim 13, further comprising forcibly ending reproduction of the animation on the terminal unit that has received the second input operation when a terminal unit among the other terminal units except the terminal unit that has received the second input operation receives the third input operation.

15. The object monitoring method according to claim 12, further comprising forcibly ending reproduction of the animation on the terminal unit that has received the second input operation when a terminal unit among the other terminal units except the terminal unit that has received the second input operation receives the third input operation.

16. The object monitoring method according to claim 11, further comprising forcibly ending reproduction of the animation on the terminal unit that has received the second input operation when a terminal unit among the other terminal units except the terminal unit that has received the second input operation receives the third input operation.

17. The object monitoring method according to claim 1, further comprising forcibly ending reproduction of the animation on the terminal unit that has received the second input operation when a terminal unit among the other terminal units except the terminal unit that has received the second input operation receives the third input operation.

* * * * *